US012734242B2

(12) United States Patent
Vrabel et al.

(10) Patent No.: US 12,734,242 B2
(45) Date of Patent: Sep. 15, 2026

(54) CARBOHYDRATE DERIVATIVES AND KITS FOR CELL SURFACE LABELING

(71) Applicant: INSTITUTE OF ORGANIC CHEMISTRY AND BIOCHEMISTRY AS CR, V. V. I., Prague (CZ)

(72) Inventors: Milan Vrabel, Galanta (SK); Rastislav Dzijak, Mosurov (SK); Anna Kovalova, Prague (CZ)

(73) Assignee: INSTITUTE OF ORGANIC CHEMISTRY AND BIOCHEMISTRY AS CR, V. V. I., Prague (CZ)

( * ) Notice: Subject to any disclaimer, the term of this patent is extended or adjusted under 35 U.S.C. 154(b) by 476 days.

(21) Appl. No.: 18/572,013

(22) PCT Filed: Jun. 20, 2022

(86) PCT No.: PCT/CZ2022/050058

§ 371 (c)(1),
(2) Date: Dec. 19, 2023

(87) PCT Pub. No.: WO2022/268239

PCT Pub. Date: Dec. 29, 2022

(65) Prior Publication Data

US 2024/0293556 A1 Sep. 5, 2024

(30) Foreign Application Priority Data

Jun. 24, 2021 (EP) .................................... 21181606

(51) Int. Cl.

*A61K 47/54* (2017.01)
*C07H 7/04* (2006.01)
*C12N 5/00* (2006.01)

(52) U.S. Cl.

CPC .......... *A61K 47/549* (2017.08); *A61K 47/545* (2017.08); *C07H 7/04* (2013.01); *C12N 5/0006* (2013.01)

(58) Field of Classification Search

None

See application file for complete search history.

(56) References Cited

FOREIGN PATENT DOCUMENTS

| | | | |
|---|---|---|---|
| EP | 3 595 719 | A1 | 1/2020 |
| EP | 2627358 | A1 | 1/2020 |
| WO | 2012049624 | A1 | 4/2012 |
| WO | 2014/205126 | A1 | 12/2014 |
| WO | 2015/114023 | A1 | 8/2015 |
| WO | 2020/256546 | A1 | 12/2020 |
| WO | 2021/119268 | A1 | 6/2021 |

OTHER PUBLICATIONS

Jan-Philip Meyer et al.; "Bioorthogonal Masking of Circulating Antibody-TCO Groups Using Tetrazine-Functionalized Dextran Polymers"; Bioconjugate Chemistry, Feb. 9, 2018; 29(2):538-545.

Raffaella Rossin et al.; "In Vivo Chemistry for Pretargeted Tumor Imaging in Live Mice"; Angewandte Chemie (International Edition), Wiley-VCH Verlag Gmbh & Co, DE, Apr. 26, 2010; 49(19):3375-3378.

Sminia Tjerk J et al.; "Getting a grip on glycans: A current overview of the metabolic oligosaccharide engineering toolbox"; Carbohydrate Research, Pergamon, GB, Sep. 16, 2016; 435:121-141.

Laughlin S T, et al.; "Metabolic Labeling of Glycans with Azido Sugars for Visualization and Glycoproteomics"; Biomembranes: Transport Theory : Cells and Model Membranes; Glycobiology; [Methods in Enzymology, ISSN 0076-6879], Elsevier, Academic Press, NL, Nov. 14, 2006; 415:230-250.

International Search Report and Written Opinion for PCT Application No. PCT/CZ2022/050058, mailed Oct. 24, 2022.

International Application Status Report generated Oct. 27, 2023.

Mareen Pagel et al. "On-resin Diels-Alder reaction with inverse electron demand: an efficient ligation method for complex peptides with a varying spacer to optimize cell adhesion"; Organic & Biomolecular Chemistry, Jun. 7, 2016; pp. 4761-4960.

*Primary Examiner* — Patrick T Lewis

(74) *Attorney, Agent, or Firm* — Notaro, Michalos & Zaccaria P.C.

(57) ABSTRACT

Carbohydrate derivatives of general formula I bearing a trans-cyclooctene moiety in covalently binding active moieties to cell surfaces in vitro and/or in vivo for therapeutic or nontherapeutic purposes are described. Compounds of general formula II are used together with the derivatives of general formula I in a method of binding active moieties to the cell surface. The compounds may be combined to form a kit for forming a covalent attachment of active moieties to the cell surface.

I

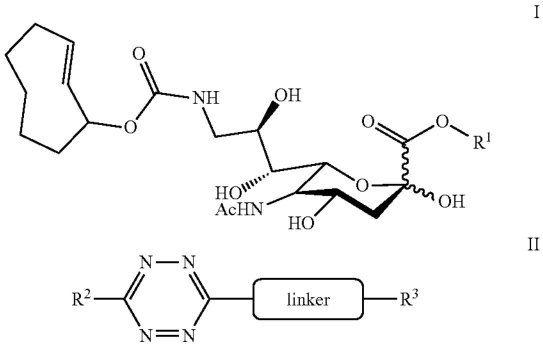

II

10 Claims, 13 Drawing Sheets

Specification includes a Sequence Listing.

A)

B)

PC3 cells + TCO-Sia
+ MeTz-Peg3-Peg3-biotin-
-Peg3-DBCO conjugate

PC3 cells + TCO-Sia
+ MeTz-Peg3-Peg3-biotin-
-Peg3-DBCO conjugate
+ Cy3-azide

PC3 cells + TCO-Sia
+ MeTz-Peg3-Peg3-biotin-
-Peg3-DBCO conjugate
+ Cy3-azide
+ streptavidin Control cells
(no FLAG-MeTz only
anti-FLAG antibody)

TCO-Sia +
FLAG-MeTz
+ anti-FLAG antibody

Control cells
(no biotin-Peg3-diPy-Tz
+ streptavidin)

TCO-Sia +
biotin-Peg3-diPy-Tz
+ streptavidin

A) Confocal microscope

B) FACS analysis

SEQUENCE LISTING

```
<160> NUMBER OF SEQ ID NOS: 2

<210> SEQ ID NO 1
<211> LENGTH: 17
<212> TYPE: DNA
<213> ORGANISM: artificial
<220> FEATURE:
<223> OTHER INFORMATION: synthetic commercial oligonucleotide

<400> SEQUENCE: 1

ttgaataagc tggtaat                                                  17


<210> SEQ ID NO 2
<211> LENGTH: 18
<212> TYPE: DNA
<213> ORGANISM: artificial
<220> FEATURE:
<223> OTHER INFORMATION: synthetic commercial oligonucleotide

<400> SEQUENCE: 2

ataccagctt attcaatt                                                 18
```

CARBOHYDRATE DERIVATIVES AND KITS FOR CELL SURFACE LABELING

FIELD OF ART

The present invention relates to chemical engineering of cell surfaces. In particular, the invention relates to carbohydrate derivatives for use in cell surface engineering.

STATEMENT ON FINANCIAL SUPPORT

The project leading to this application received funding from the European Research Council (ERC) under the European Union's Horizon 2020 research and innovation programme (grant agreement No 677465).

BACKGROUND ART

The cell surface is a complex environment made of lipids, proteins and carbohydrates. These components are involved in numerous physiological functions, and directly influence the communication and interaction of the cells with the external environment. The attachment of additional moieties to the surface of cells can endow cells with new properties and functions. Such modified cells find utility in numerous fields, including: bioimaging, biomaterials, regenerative medicine, drug delivery systems, immunotherapy and other biomedical applications.

Various genetic manipulations and enzymatic methods can be used to tailor the composition of the cell surface. Beyond these molecular biology techniques, advances in engineering and materials science enable the attachment of additional, non-encodable moieties to the cell surface (Zhao et al. Materials Today 13(4): 14, 2010). Among these, the covalent attachment of different moieties to the components of the cell surface is the preferred option over the non-covalent, physical attachment methods, due to the enhanced stability/durability provided by the covalent chemical bonds (Custódio et al. Chem Nano Mat, 2(5): 376, 2016 and Thomsen et al. ACS Applied Bio Materials, 4(3): 2293, 2021). However, the traditional methods based on the chemical reactivity of natural functional groups present on the cell surface (usually amines and thiols) (Fox et al. Chapter 2 in Micro- and Nanoengineering of the Cell Surface, Elsevier, William Andrew Publishing: Oxford, ISBN: 9781455731558, 2014) are often difficult to control and result in the random modification of various cell surface components that can negatively affect the viability and function of the cells. An alternative approach is based on the attachment of non-natural functional groups which can be used in the second step for the modification of the cell surface via a selective, biocompatible chemical reaction (Sminia et al. Carbohydrate Research, 435: 121, 2016 and Agatemor et al. Nature Reviews Chemistry, 3 (10): 605, 2019). A prominent example of such an approach is the metabolic integration of azidosugars into cellular glycoconjugates, which can be used for the attachment of different molecules to cell surfaces via Cu-catalyzed click reaction, via metal-free Staudinger ligation or strain-promoted azide alkyne cycloaddition (Laughlin et al. Methods in Enzymology, 415: 230, 2006). There are also alternative chemical modifications of cell surfaces based on the incorporation of unnatural carbohydrates followed by a click reaction (Sminia et al. Carbohydrate Research, 435: 121, 2016). However, these reactions require the use of toxic metals (e.g. copper) (Kennedy et al. Journal of the American Chemical Society, 133 (44): 17993, 2011), unstable reagents (e.g. phosphines, strained alkynes), they often lead to non-specific background labeling (van Geel et al. Bioconjugate Chemistry, 23 (3): 392, 2012) and require the use of a large excess of labeling reagents to overcome the slow reaction rates. These make the methods either unsuitable for modification of live cells or make the modification procedure problematic, time consuming and expensive.

DISCLOSURE OF THE INVENTION

This invention addresses many of the challenges and limitations of the currently used methods for cell surface engineering. Provided herein are carbohydrate derivatives that are metabolically processed by various cell lines to attach trans-cyclooctene (TCO) chemically reactive molecules to the cell surfaces. The TCO groups then enable subsequent attachment of various active moieties in a modular and highly efficient manner to cell surfaces by forming stable covalent bonds in reaction with tetrazine conjugates (schematically shown in FIG. 9).

The present invention provides a carbohydrate derivative of general formula I:

I

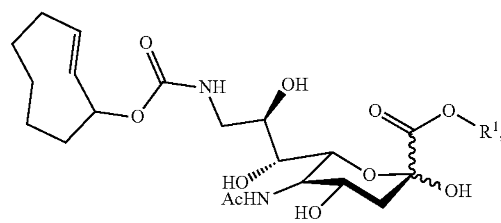

wherein $R^1$ is selected from H, $C_{1-6}$ linear or branched alkyl.

The C—O bond between the trans-cyclooctene and the carbamate may be axial or equatorial in relation to the trans-cyclooctene moiety, preferably it is axial.

The invention further relates to the carbohydrate derivative of general formula I as described above for use in covalently binding active moieties to cell surfaces in vivo for therapeutic purposes.

The invention further relates to use of the carbohydrate derivative of general formula I as described above for covalently binding active moieties to cell surfaces in vitro.

The invention further relates to a tetrazine conjugate of general formula II

II

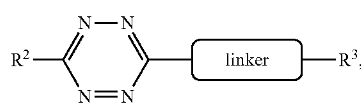

wherein $R^2$ is selected from: H, $C_{1-10}$ alkyl, $C_{6-10}$ aryl, 5-10-membered heteroaryl, $C_{1-10}$ alkoxy, $C_{6-10}$aryl-$C_{1-10}$alkyl, 5-10-membered heteroaryl-$C_{1-10}$alkyl;

linker is selected from $C_{1-10}$ alkylene, $C_{6-10}$ arylene, 5-10-membered heteroarylene, $C_{6-10}$aryl-$C_{1-10}$alkylene, 5-10-membered heteroaryl-$C_{1-10}$alkylene, and PEG;

$R^3$ is an active moiety selected from fluorophore, inhibitor, ligand, oligonucleotide, peptide, protein, enzyme, antibody, single-domain antibody, polymer, and nanoparticle;

for use in covalently binding active moieties to cell surfaces in vivo for therapeutic purposes.

Preferably, $R^2$ is selected from H, $C_{6-10}$ aryl, $C_{5-10}$ heteroaryl.

Preferably, linker is 5-10-membered heteroaryl-$C_{1-10}$alkylene or PEG.

The invention further relates to use of the tetrazine conjugate of general formula II as described above for covalently binding active moieties to cell surfaces in vitro.

The invention further relates to use of the tetrazine conjugate of general formula II as described above for covalently binding active moieties to cell surfaces in vivo for nontherapeutic purposes.

Unless defined otherwise, all technical and scientific terms used herein have the same meaning as commonly understood by one of ordinary competence in the field. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or "$C_u$-$C_v$" indicates that the following group has from u to v carbon atoms, wherein u and v are integers. For example, "$C_{1-6}$ alkyl" or "$C_1$-$C_6$ alkyl" indicates that the alkyl group has from 1 to 6 carbon atoms. An indication such as "u-v-membered" indicates that the following group has from u to v atoms, wherein u and v are integers.

"Ac" means acetyl.

"Alkyl" is a linear or branched saturated monovalent hydrocarbon. For example, an alkyl group can have 1 to 10 carbon atoms (i.e., $C_{1-10}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, and octyl ($—(CH_2)_7CH_3$). Alkyl groups can be unsubstituted or substituted.

"Alkoxy" refers to the group —O-alkyl, wherein alkyl is as defined above. For example, $C_{1-4}$ alkoxy refers to an —O-alkyl group having 1 to 4 carbons.

"Aryl" refers to aromatic cyclic compounds having 6 to 10 carbon atoms. Aryl groups include, but are not limited to, groups such as phenyl, substituted phenyl, naphthyl, substituted naphthyl, in which the substituent is preferably alkyl or halogen.

"Heteroaryl" for the purposes of the present application refers to a monocyclic or multicyclic ring system, having preferably 5 to 10 members, in which at least one atom, preferably 1 to 3 atoms, is a heteroatom, which is an element other than carbon, including nitrogen, oxygen, or sulfur atoms. At least one ring of the heteroaryl is aromatic. The heteroaryl may be optionally substituted with one or more, preferably 1 to 3, aryl or alkyl group substituents. Examples of heteroaryl groups include, but are not limited to, furanyl, thienyl, pyridyl, pyrrolyl, N-methylpyrrolyl, quinolyinyl and isoquinolinyl.

"Aryl-alkyl" as used herein refers to an alkyl group which is substituted with one or more aryl groups. Examples of aryl-alkyl groups include, but are not limited to, benzyl, 9-fluorenylmethyl, naphthylmethyl, diphenylmethyl, and triphenylmethyl.

"Heteroaryl-alkyl" as used herein refers to an alkyl group which is substituted with one or more heteroaryl groups. Examples of heteroaryl-alkyl groups include, but are not limited to, pyridylmethyl, pyrimidinylmethyl, imidazolemethyl, and quinolinemethyl.

"PEG" refers to polyethylene glycol, which is a linear or branched polymer composed of repeating units. PEG can be described by a formula $H(OCH_2CH_2)_nOH$ wherein n=3-30. Examples of PEG include, but are not limited to triethyleneglycol (PEG3), tetraethyleneglycol (PEG4), pentaethyleneglycol (PEG5), and dodecaethyleneglycol (PEG12).

"Alkylene" refers to a straight, branched, or cyclic, preferably straight or branched, bivalent aliphatic hydrocarbon group; preferably having from 1 to 10 carbon atoms. The alkylene group is optionally substituted with one or more alkyl group substituents. One or more carbon atoms can optionally be replaced by one or more oxygen, sulfur, or substituted or unsubstituted nitrogen atoms, wherein the nitrogen substituent is alkyl or aryl. Preferably, 1-4 carbon atoms are thus replaced. Examples of alkylene groups include methylene, ethylene, propylene, cyclohexylene, methylenedioxy, and ethylenedioxy.

"Arylene" as used herein refers to a monocyclic or polycyclic bivalent aromatic group preferably having from 6 to 10 carbon atoms and at least one aromatic ring. The arylene group is optionally substituted with one or more alkyl group substituents. Examples of arylene groups include, but are not limited to, phenylene, naphtylene, anthrylene, and phenantrylene.

"Heteroarylene" refers to a bivalent monocyclic or multicyclic ring system, preferably of about 5 to about 10 members, wherein one or more of the atoms in the ring system is a heteroatom, and wherein at least one ring is aromatic. The heteroarylene may be optionally substituted with one or more, preferably 1-3, aryl or alkyl substituents. The heteroatoms are typically selected from oxygen, sulfur, or substituted or unsubstitued nitrogen atoms, wherein the nitrogen substituent is alkyl or aryl. Examples of arylene groups include, but are not limited to, pyridylene and pyrimidylene.

"Unnatural" is any variation in the structure of a compound or biopolymer typically not found in nature. This includes the addition of substituents or atoms, removal of substituents or atoms, or other structural changes that differ from those found in natural compounds, natural building blocks and natural biopolymers. Examples of unnatural as used in the present disclosure include amino acids with unnatural D-configuration (D-amino acids), chemically synthesized non-proteinogenic amino acids (examples can be found in https://www.sigmaaldrich.com/chemistry/chemistry-products.html?TablePage=16274965), and modified nucleic acids containing unnatural modifications such as those described in Ochoa et al. Molecules 25: 4659, 2020.

"Fluorophore" is a molecule that, when excited with light of a selected wavelength, emits light of a different wavelength, which may emit light immediately or with a delay after excitation. Fluorophores include, but are not limited to, fluorescein dyes, e.g., 6-carboxyfluorescein (6-FAM), 5-carboxyfluorescein (5-FAM), 2',4',5',7',1,4-hexachlorofluorescein (HEX), 2',4',1,4,-tetrachlorofluorescein (TET), and 2',7'-dimethoxy-4',5'-dichloro-6-carboxyfluorescein (JOE); cyanine dyes, e.g. Cy3, Cy5, Cy5.5, Cy7 etc.; dansyl derivatives; rhodamine dyes e. g. CAL FLUOR dyes, 6-carboxytetramethylrhodamine (TAMRA), Janelia fluor dyes, tetrapropano-6-carboxyrhodamine (ROX). BODIPY fluorophores, pyrene, ALEXA dyes, Oregon Green, perylene, benzopyrene, squaraine dyes, coumarin dyes, luminescent transition metal and lanthanide complexes and the like.

"Inhibitor" is a substance that slows down or interferes with a chemical action, or a substance that reduces or suppresses the activity of another substance (such as an enzyme). The inhibitor may function by combining with the enzyme at the site at which the substrate usually combines (competitive inhibition) or at some other site (noncompetitive inhibition). In the latter, the inhibitor does not prevent the binding of the substrate to the enzyme, but sufficiently changes the shape of the site at which catalytic activity occurs so as to prevent it. Irreversible inhibitors are those that permanently disable the enzyme. Preferably, the inhibitor is chosen from compounds that act on and bind cell surface biomolecules such as proteins, enzymes, cancer biomarkers or cell surface receptors with high affinity (equal or less than 100 μM). Examples of inhibitors include, but are not limited to, inhibitors of EGFR, e.g. erlotinib, afatinib, PKI-166, mavelertinib, cyasterone, icotinib, naquotinib, AV-412, olafertinib, and zorifertinib; inhibitors of carbonic anhydrases (CA), preferably inhibiting CA-IX and CA-XII isoforms, e.g. sulfonamide inhibitors such as acetazolamide, zonisamide, ethoxzolamide, 2-aminobenzenesulfonamide, sultiame, dichlorphenamide, and brinzolamide; inhibitors of HER2, e.g. pyrotinib, tarloxotinib, BDTX-189, mubritinib, tucatinib, neratinib, and varlitinib; inhibitors of fibroblast activation protein (FAP), e.g. FAPI-2, FAPI-4, and talabostat; inhibitors of carboxypeptidases (for example glutamate carboxypeptidase II or III, GCPII or GCPIII), e.g. glutamate ureido-based inhibitors, 2-PMPA, 2-MPPA, JHU 241, and ZJ-43.

"Ligand" is a substance (e.g. hormone, drug, functional group, etc.) that binds specifically and reversibly to another chemical entity to form a larger complex. A ligand often binds with a biological molecule to form a complex and produce an effect; the term frequently refers to substances that bind to receptors. The formation of a protein-ligand complex is based on molecular recognition between biological macromolecules and ligands, wherein ligand means a molecule that binds to the protein with high affinity (equal to or less than 100 μM) and specificity. A wide range of ligands can be found in the ligand-protein binding database BioLip (https://zhanglab.dcmb.med.umich.edu/BioLiP/). Frequently used biologically relevant ligands include, but are not limited to, glycinate, heme, aminopolycarboxylic acids, chlorothiazide, benzothiadiazine, methazolamide, multi-targeted platinum-group metal complexes, folic acid, biotin, desthiobiotin, anisamide, interleukins, interferons, selectin-binding ligands, and steroids.

"Oligonucleotide" is a compound composed of nucleosides and/or nucleotides joined by phosphate backbones. Oligonucleotides include DNA, RNA (single- or double-stranded), and includes unnatural modifications in the purine or pyrimidine nucleobase(s), deoxyribose or ribose unit(s) or in the phosphate backbone, such as those described in Ochoa et al. Molecules 25: 4659, 2020. Modified oligonucleotides include peptide nucleic acid (PNA), in which the deoxyribose or ribose of natural oligonucleotides is replaced by repeating N-(2-aminoethyl)-glycine units linked by peptide bonds. Preferred examples of oligonucleotides that find use in the present disclosure include aptamers: Macugen, AS1411, Sgc8, TD05, ARC1779, ARC1905, ARC19499, E10030, NOX-E36, NOX-A12, NOX-H94, NU172, REG1, TBA and those described in Zhu et al. Chem Med Chem 10(1): 39, 2015) and Sun et al. Molecular Therapy Nucleic Acids 3: e182, 2014.

"Peptide" is a biopolymer composed of 2-20 amino acids selected from L-amino acids and/or unnatural D-amino acids, joined via peptide bonds. The peptide is typically produced via liquid-phase or solid-phase peptide synthesis, and can be linear or cyclized in structure. Examples of preferred peptides that find use in the present disclosure include, but are not limited to, SRL, GFE-1, GFE-2, SMS, RGD-4C, iRGD, cRGDfK, NGR, F3, Lyp-1, Lyp-2, LSD, REA, AGR, RSR, KAA, RGR, KRK and those described in Laakkonen et al. Integrative Biology 2(7-8): 326, 2010; Aina et al. Molecular Pharmaceutics 4(5): 631, 2007.

"Protein" is a biopolymer composed of more than 20 L-amino acids and/or unnatural D-amino acids joined via peptide bonds. The protein can contain additional modifications such as glycosylation (glycoprotein), phosphorylation, or linear or branched fatty acids. Preferably, the protein is chosen from biopolymers which bind other biopolymers or molecules onto cell surfaces (e.g. carbohydrates). Examples of proteins that find use in the present disclosure include, but are not limited to, lectins, sialic acid-binding immunoglobulin-type lectins (Siglecs), and selectins.

"Enzyme" is a biopolymer composed of L-amino acids and/or unnatural D-amino acids joined via peptide bonds and having enzymatic activity by which it converts substrates into products. Preferably, the enzyme is a target cell surface-editing enzyme. As used herein, a "target cell surface-editing enzyme" is an enzyme which, upon binding to the corresponding cell surface, causes a structural change in one or more molecules on the cell surface by removing or adding additional molecules to the cell surface. Examples of cell surface-editing enzymes include, but are not limited to, enzymes cleaving carbohydrates such as glycosidases, e.g. sialidase/neuraminidase, galactosidase, mannosidase, and glucosidase; enyzmes removing phosphate groups, e.g. phosphatases; enzymes adding carbohydrates to molecules on cell surfaces such as glycosyltransferases, e.g. sialyltransferase and fucosyltransferase; enzymes adding phosphate groups, e.g. kinases.

"Antibody" is a biopolymer that binds a specific antigen or tumor-associated cell surface molecule or tumor-specific cell surface molecule onto the surface of a cancer cell. The antibody is preferably selected from therapeutic antibodies including, but not limited to, trastuzumab, cetuximab, rituximab, daratumumab, ofatumumab, panitumumab, girentuximab, and antigen-binding variants thereof.

"Single-domain antibody" is a biopolymer that binds a specific antigen onto cells and is usually a single-chain variant of an antibody.

"Polymer" is a substance or material made of molecules, macromolecules and consisting of repeating subunits that can contain additional functional groups. As used herein, the polymer is preferably selected from synthetic substances such as polyethyleneglycol (PEG), polyvinyl alcohol, polyethyleneimine, polyallylamine, polystyrene, hyaluronic acid, or N-(2-hydroxypropyl) methacrylamide (HPMA) copolymer. The additional functional groups include additional hydrophilic or hydrophobic functional molecules such as e.g. lipids, carbohydrates, phosphate groups or sulfo groups.

"Nanoparticle" is a particle having at least one dimension in the range of 1 nm to 1000 nm, preferably 20 nm to 750 nm, more preferably 50 nm to 500 nm, including 100 nm to 300 nm, e.g., 120-200 nm. The nanoparticle may have a geometric shape or a non-geometric shape. Examples of geometric shapes include spherical, spheroid, rod-shaped, disk-shaped, pyramid-shaped, cube-shaped, cylinder-shaped, nanohelical-shaped, nanospring-shaped, nanoring-shaped, arrow-shaped, teardrop-shaped, tetrapod-shaped, prism-shaped. Non-geometric shapes are irregular shapes or shapes that cannot be described as geometric bodies. In certain aspects, the nanoparticle includes on its surface one or more of the other active moieties described herein, e.g., a fluorophore, antibodies, ligands, aptamers, etc. Nanoparticles that find use in the present disclosure include, but are not limited to, dendrimers, liposomes, polymeric nanoparticles, micelles, protein nanoparticles, ceramic nanoparticles, viral nanoparticles, metallic nanoparticles, carbon nanotubes and those described in Wang et al. Pharmacological Research 62(2): 90, 2010; Rao et al. ACS Nano 9(6): 5725, 2015; and Byrne et al. Advanced Drug Delivery Reviews 60(15):1615, 2008.

The cells amenable to modification by the carbohydrates are preferably selected from cancer cells, epithelial cells, endothelial cells, fibroblasts, stem cells, immune cells, macrophages, blood cells and monocytes. More specific examples include, but are not limited to, U2OS, HeLa, THP1, Raji, Jurkat, MDCK, NK-cells, and PBMCs.

The invention further relates to a method of binding active moieties to a cell surface comprising the following steps:

a) cells are co-cultured with at least one TCO-containing carbohydrate of general formula I to form trans-cyclooctene presenting cells;
b) at least one 1,2,4,5-tetrazine conjugate of general formula II containing an active moiety is brought into contact with the trans-cyclooctene presenting cells in order to covalently attach the said active moiety to the cell surface.

The method is preferably an in vitro method.

The method is preferably for non-therapeutic purposes.

In step a), the cells metabolize the one or more TCO-containing carbohydrates of general formula I via the metabolic pathway of sialic acid/N-acetylneuraminic acid, which results in the attachment of the TCO groups onto the cell surface, thus forming cells presenting trans-cyclooctene on their surface.

In step b), at least one 1,2,4,5-tetrazine conjugate of general formula II containing an active moiety is brought into contact with the trans-cyclooctene presenting cells. This steps results into Diels-Alder cycloaddition reaction of the tetrazine moiety with the trans-cyclooctene moiety, thus covalently attaching the said active moiety to the cell surface via the cycloaddition product. This type of reaction is called tetrazine-trans-cyclooctene ligation.

In a preferred embodiment, the reaction in step b) between the TCO groups on the cell surface and the added tetrazine conjugates is carried out at a temperature within the range of room temperature (20° C.) to 37° C. in the cell culturing medium or in a biologically acceptable buffer (e.g. phosphate-buffered saline, PBS), typically within 30 minutes.

The present invention further relates to a kit comprising at least one TCO-containing carbohydrate of general formula I and at least one 1,2,4,5-tetrazine conjugate of general formula II.

Yet furthermore, the present invention relates to a kit containing at least one TCO-containing carbohydrate of general formula I, cells amenable to modification by the said carbohydrates, and at least one 1,2,4,5-tetrazine conjugate of general formula II.

The kits enable a covalent attachment of active moieties comprised in the 1,2,4,5-tetrazine conjugate(s) to a cell surface in a practical and easy way.

Biologically acceptable buffers are aqueous solutions that maintain a constant pH over a given range by neutralizing the effects of hydrogen ions. Examples of such buffers include, but are not limited to, phosphate-buffered saline (PBS), 4-(2-hydroxyethyl)-1-piperazineethanesulfonic acid (HEPES), Tris/Borate/EDTA buffer, and others. See for example Goldberg et al., J. Phys. Chem. 31(2): 231, 2002 or Good et al., Biochemistry 5(2): 467, 1966.

The present invention has the following advantages: the carbohydrate derivatives of general formula I enable a robust attachment of the artificial trans-cyclooctene groups onto the surface of living cells. The group is attached into glycoconjugates such as glycoproteins or glycolipids. The attachment results in no apparent toxicity nor any other negative effects on cell viability and cell functionality. The subsequent modification step by tetrazine conjugates does not require use of toxic reagents or catalysts. The modification step is simple, consisting only in addition of the tetrazine conjugate to cells, proceeds at fast rates (typically 30 min reaction), requires low concentrations of the reagents, does not require any genetic manipulations nor use of additional enzymes, and enables the production of variously modified/engineered cells with high commercial value at low cost.

Depending on the intended application, the resulting cell-surface modified cells can be used for bioimaging, for construction of biomaterials, in regenerative medicine, as drug delivery systems, in immunotherapy and other biomedical applications.

Examples of preferred uses of the present invention include bioimaging, wherein the labeling of cells with a suitable fluorophore, dye or other imaging probe is used to track the biodistribution of the cells in vivo. Preferably such applications include cell tracking, wherein the biodistribution of therapeutic cells is performed as a critical part of safety and efficacy process before the therapeutic use of the cells. An example of the use of the modified cells also includes the attachment of drug molecules to cells wherein the cells are used as a drug delivery system to enhance cancer therapy by transporting the therapeutic molecules to cancer tissues. Applications in immunotherapy include the modification of immune cells (e.g. T-cells, NK-cells) with targeting moieties (e.g. antibodies, aptamers, targeting ligands), which direct the immune cells to e.g. cancer cells in vivo, thereby enhancing the therapeutic effect of immune cells.

LIST OF ABBREVIATIONS

Figure 1:
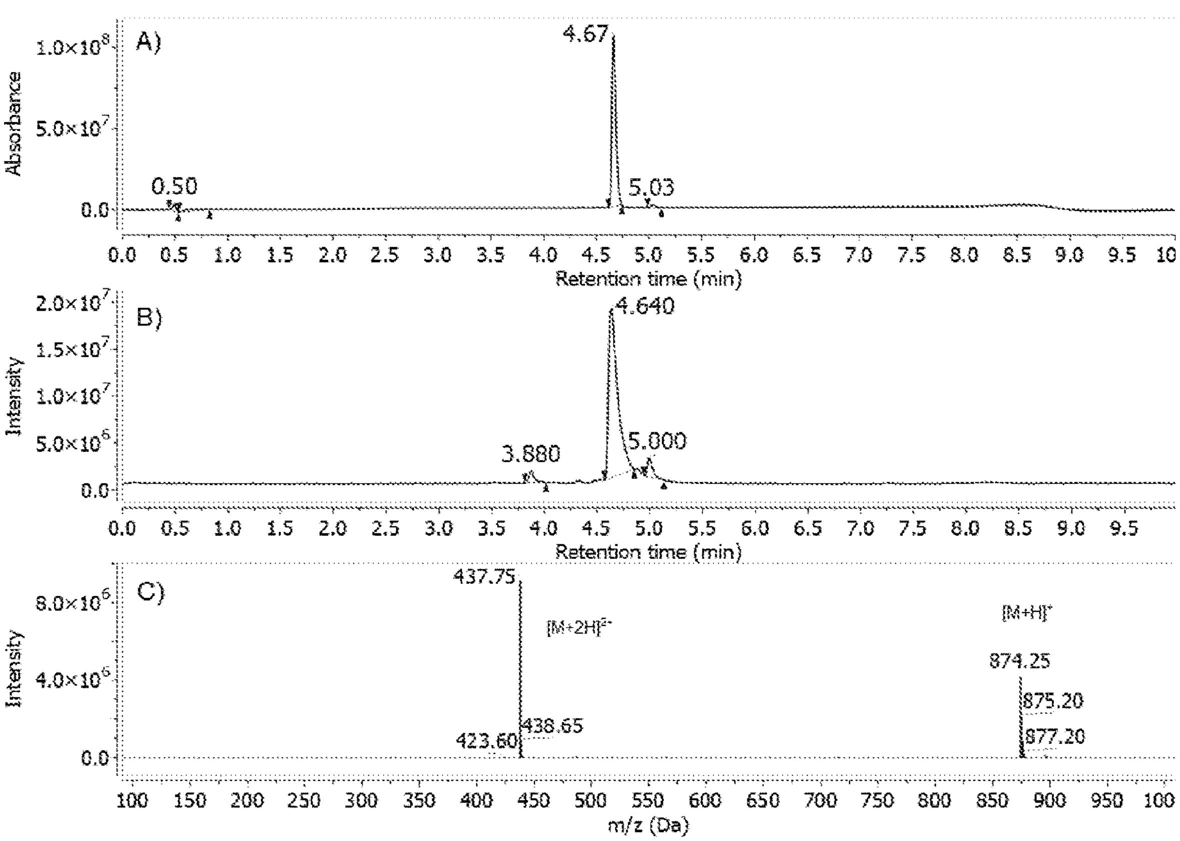
FIG. 1: HPLC-MS analysis of sulfonamide-PEG3-diPyTz conjugate. A) PDA total absorbance chromatogram, B) TIC (total ion count) chromatogram, C) extracted m/z from signal at 4.64 min.

TCO=trans-cyclooctene, Tz=1,2,4,5-tetrazine, PEG=polyethyleneglycol, DNA=deoxyribonucleic acid, RNA=ribonucleic acid, PNA=peptide nucleic acid, U2OS=human bone osteosarcoma epithelial cells, HeLa=human cervical cancer cells, THP1=human acute monocytic leukemia cells, Raji=human Burkitt's lymphoblast cells, Jurkat=human T cell leukemia cells, MDCK=Madin-Darby Canine Kidney cells, NK=natural killer cells, PBMC=human peripheral blood mononuclear cells, ATCC=American Type Culture Collection, HPLC=high-performance liquid chromatography, MS=mass spectrometry, FACS=fluorescence-activated cell sorting, NMR=nuclear magnetic resonance, RP=reversed phase, h=hours, MeOH=methanol, MeOD=deuterated methanol, EtOH=ethanol, iPrOH=isopropanol, DCM=dichloromethane, DMF=N,N-dimethylformamide, DMSO=dimethylsulfoxide, $CH_3CN$=acetonitrile, HCOOH=formic acid, TFA=trifluoroacetic acid, DIPEA=N,N-diisopropylethylamine, HCl=hydrochloric acid, NaOH=sodium hydroxide, $CO_2$=carbon dioxide, Fmoc=fluorenylmethyloxycarbonyl, $H_2O$=water, NBD=7-nitrobenzo-2-oxa-1,3-diazole, NRP=neuropilin, hCA=human carbonic anhydrase, FAP=fibroblast activation protein alpha, HER2=human epidermal growth factor receptor 2, EGFR=epidermal growth factor receptor, PE=phycoerythrin, PBS=phosphate-buffered saline, FBS=fetal bovine serum, HEPES=4-(2-hydroxyethyl)-1-piperazineethanesulfonic acid, DMEM=Dulbecco's modified eagle medium, RPMI=Roswell Park Memorial Institute medium.

EXAMPLES

I. Synthesis of Carbohydrates

The chemicals were obtained from Sigma Aldrich, Alfa Aesar, Acros Organics, ABCR, Flouorochem, Iris Biochem, Carbosynth or VWR unless otherwise stated, and were used without further purification. Solutions were concentrated in a rotary evaporator from Heidolph equipped with a PC3001 VARIOpro pump from Vacuubrand. Column chromatography was carried out on silica gel 60 Å (particle size: 40-60 m) from Acros Organics. p.a.-quality solvents from Lach-Ner and Penta were used for elution. A CombiFlash® Rf+ from Teledyne ISCO was used for flash column chromatography. $^1$H- and $^{13}$C-NMR spectra were measured in a Bruker Avance III™ HD 400 MHz NMR system equipped with a Prodigy cryo-probe or in a Bruker Avance III™ HD 500 MHz Cryo. Analytical HPLC-MS measurements were performed either in an LCMS-2020 system from Shimadzu equipped with a Luna® C18(2) column (3 μm, 100 A, 100×4.6 mm), CORTECS column (C18 from Waters) or in an HPLC-MS Infinity 1260 system equipped with a 6120 Quadrupole LC/MS detector from Agilent Technologies and either a Luna® 5 μm C18 preparative column (2), 100 Å, 250×21.2 mm (Phenomenex) or Poroshell 120 analytical column, EC-C18 4 μm, 4.6×100 mm (Agilent Technologies). Automated peptide synthesis was done in a PS3™ Peptide Synthesizer, Protein Technologies, Inc.

Example 1: Preparation of methyl (4S,6R)-5-acetamido-6-((1R,2R)-3-(((((E)-cyclooct-2-en-1-yl)oxy)carbonyl)amino)-1,2-dihydroxypropyl)-2,4-dihydroxytetrahydro-2H-pyran-2-carboxylate (TCO-SiaOMe)

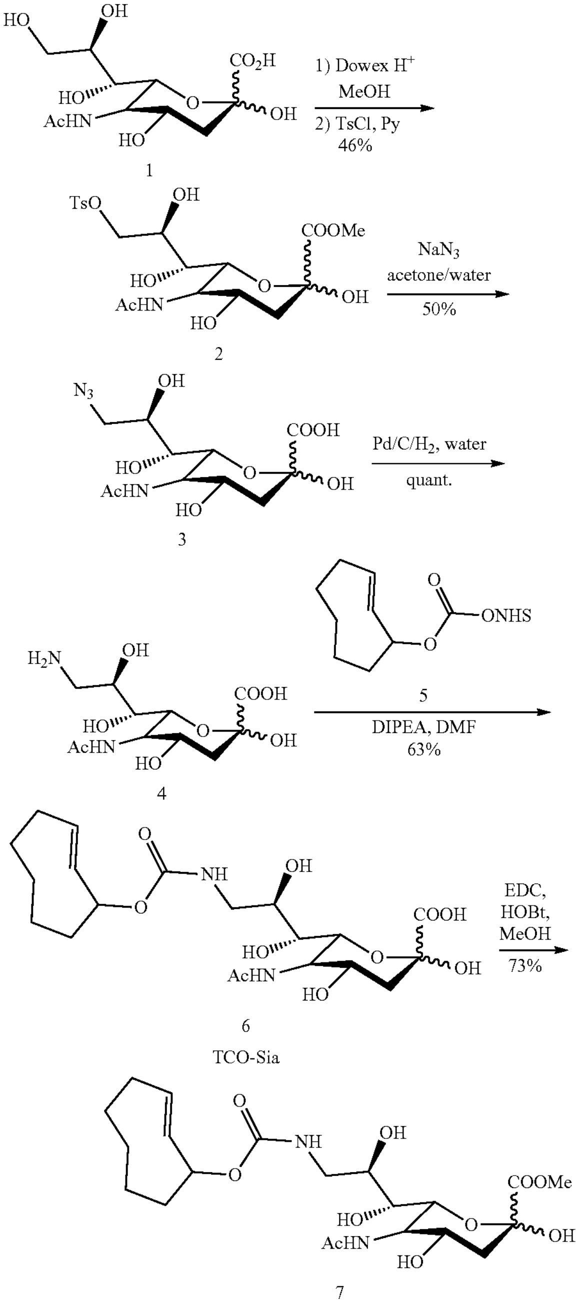

1 2 3 4 6 TCO-Sia 7 TCO-SiaOMe

1. Freshly prepared Dowex 50 W×8 in $H^+$ cycle (2 g) was added to sialic acid (1) (5 g) dissolved in dry MeOH (100 mL), and the mixture was stirred under an argon atmosphere for 30 hours. The resulting clear solution of the product was concentrated under vacuum to yield the methyl ester of sialic acid as an off-white solid. The methyl ester of sialic acid was dissolved in dry pyridine (50 mL), and the mixture was cooled down on ice before paratoluenesulfonyl chloride (3.2 g) was added to the solution in portions. After stirring for 18 hours, the solvent was removed under vacuum and the residue was further dried under high vacuum. The resulting crude product was purified by silica gel column chromatography (using a gradient of MeOH in DCM) to obtain the product (2) as a white solid, which was used without further purification in the next step.
2. Sodium azide (0.41 g) was added to compound (2) (0.75 g) dissolved in acetone/water mixture (3/1, 12 mL), and the resulting mixture was stirred at 70° C. for 15 hours. After cooling down to room temperature, the solvents were removed under vacuum and the residue was co-evaporated with EtOH and further dried under high vacuum. The crude reaction product was purified by C18 flash column chromatography (using a gradient of $CH_3CN$ in water, both containing 0.05% HCOOH). The product (3) was isolated as a beige solid after lyophilization, and was used without further purification in the next step.
3. Pd/C (20 mg) was added to compound (3) (0.26 g) dissolved in water (8 mL), and the flask was purged with $H_2$ gas. The mixture was stirred under an $H_2$ atmosphere at room temperature for 6 hours. The crude reaction mixture was passed through a pad of celite to remove Pd/C, and the resulting aqueous solution was lyophilized to yield product 4 as a beige solid, which was used without further purification in the next step.
4. TCO-NHS active ester (TCO-N-hydroxysuccinimide, 5, from SiChem, SC-8070) (105 mg) at 0° C. was added to compound (4) (0.15 g) dissolved in dry dimethylformamide (4.5 mL), followed by DIPEA (diisopropylethylamine) (340 μL). The reaction mixture was stirred at room temperature for 5 hours. The reaction was quenched by the addition of water (0.5 mL), and the reaction mixture was stirred at room temperature for 30 minutes. The solvents were evaporated under reduced pressure, and the residue was purified by C18 flash column chromatography (using a gradient of $CH_3CN$ in water, both containing 0.05% HCOOH). The product TCO-Sia (6) was obtained as a colorless solid after lyophilization (mixture of anomers). $^1H$ NMR (600.1 MHz, MeOD): 0.83-0.91 (m, 1H); 1.13-1.20 (m, 1H); 1.46-1.53 (m, 1H); 1.60-1.68 (m, 1H); 1.69-1.76 (m, 1H); 1.82 (dd, 1H, $J_{gem}$=12.8, $J_{3b,4}$=11.6); 1.83-1.90 (m, 1H); 1.95-2.07 (s, 6H, $CH_3CO$); 2.21 (dd, 1H, $J_{gem}$=12.0, $J_{3a,4}$=4.9); 2.42-2.48 (m, 1H); 3.15-3.32 (m, 1H); 3.39 (bd, 1H, $J_{7,8}$=9.5); 3.546, 3.552 (2×dd, 2×1H, $J_{gem}$=14.2, $J_{9a,8}$=5.3); 3.71-3.76 (m, 1H); 3.84 (t, 1H, $J_{5,4}$=$J_{5,6}$=10.4); 4.012, 4.014 (2×dd, 2×1H, $J_{6,5}$=10.4, $J_{6,7}$=1.3); 4.03 (ddd, 1H, $J_{4,3}$=11.6, 4.9, $J_{4,5}$=10.4); 5.23-5.27 (m, 1H); 5.55 (dd, 1H, $J_{2,3}$=16.4, $J_{2,1}$=2.2); 5.82-5.89 (m, 1H). $^{13}C$ NMR (150.9 MHz, $CD_3OD$): 22.70 ($CH_3CO$); 25.20, 25.21 ($CH_2$-7-cyclooctene); 30.09 ($CH_2$-6-cyclooctene); 36.79 ($CH_2$-4-cyclooctene); 37.03 ($CH_2$-5-cyclooctene); 40.99, 41.00 ($CH_2$-3); 41.63, 41.66 ($CH_2$-8-cyclooctene); 45.40, 45.46 ($CH_2$-9); 54.24 (CH-5); 67.89 (CH-4); 70.84, 70.89 (CH-8); 71.49, 71.54 (CH-7); 72.08, 72.10 (CH-6); 75.30, 75.31 (CH-1-cyclooctene); 96.61 (C-2); 132.61, 132.64 (CH-3-cyclooctene); 132.81, 132.85 (CH-2-cyclooctene); 159.08 (OCON); 173.46 ($CH_3CO$); 174.93 (C-1).
5. A solution of 1-Hydroxybenzotriazole (HOBt) (8.8 mg in 140 μL MeOH) and a solution of N-(3-Dimethylaminopropyl)-N'-ethylcarbodiimide hydrochloride (EDC) (12.5 mg in 140 μL MeOH) at 0° C. were added to compound (6) (20 mg) dissolved in MeOH (140 μL), and the reaction was stirred at room temperature for 20 min. The crude reaction mixture was diluted with water (1.5 mL), filtered and loaded into a C18 HPLC column, where it was purified (using a gradient of $CH_3CN$ in water, both containing 0.05% HCOOH). The methyl ester of TCO-Sia (TCO-SiaOMe, 7) was isolated as a colorless solid after lyophilization (mixture of anomers). $^1$H NMR (MeOD, 400 MHz): δ=0.89 (ddd, 1H, J=3.8, 10.4, 17.9, H-6b-cyclooctene), 1.12-1.25 (m, 1H, H-7b-cyclooctene), 1.46-1.59 (m, 1H, H-5b-cyclooctene), 1.62-1.73 (m, 1H, H-7a-cyclooctene), 1.77 (ddd, 1H, J=1.7, 3.4, 13.0, H-8b-cyclooctene), 1.83-1.96 (m, 1H, H-6a-cyclooctene), 1.96-2.16 (m, 5H, CH3CO, H-4b,5a,8a-cyclooctene), 2.24 (dd, 1H, J=4.9, 12.9 Hz, H-3a), 2.47 (d, 1H, J=10.5 Hz, H-4a-cyclooctene), 3.20 (dt, 1H, J=6.6, 13.5, 1H, H-9b), 3.41 (dd, 1H, J=1.4, 8.8 Hz, H-7), 3.58 (dt, 1H, J=3.6, 14.0, H-9a), 3.70-3.84 (m, 1H, H-8), 3.80 (s, 3H, $OCH_3$), 3.81-3.88 (m, 1H, H-5), 3.99-4.11 (m, 2H, H-4, H-6), 4.59 (s, 1H), 5.27 (s, 1H, H-1-cyclooctene), 5.49-5.62 (m, 1H, H-2-cyclooctene), 5.88 (t, 1H, J=13.5, H-3-cyclooctene). $^{13}$C NMR (101 MHz, MeOD) δ=22.70 ($CH_3CO$); 25.20, ($CH_2$-7-cyclooctene); 30.09 ($CH_2$-6-cyclooctene); 36.79 ($CH_2$-4-cyclooctene); 37.02 ($CH_2$-5-cyclooctene); 40.68 ($CH_2$-3); 41.66 ($CH_2$-8-cyclooctene); 45.38 ($CH_2$-9); 53.17 ($OCH_3$); 54.30 (CH-5); 67.89 (CH-4); 70.92, 70.98 (CH-8); 71.52 (CH-7); 72.00, 72.02 (CH-6); 75.30 (CH-1-cyclooctene); 96.68 (C-2); 132.63 (CH-3-cyclooctene); 132.81 (CH-2-cyclooctene); 159.06 (OCON); 171.76 ($CH_3CO$); 174.99 (C-1).

Example 2: Preparation of ethyl (4S,6R)-5-acetamido-6-((1R,2R)-3-(((((E)-cyclooct-2-en-1-yl)oxy)carbonyl)amino)-1,2-dihydroxypropyl)-2,4-dihydroxytetrahydro-2H-pyran-2-carboxylate (TCO-SiaOEt) and isopropyl (4S,6R)-5-acetamido-6-((1R,2R)-3-(((((E)-cyclooct-2-en-1-yl)oxy)carbonyl)amino)-1,2-dihydroxypropyl)-2,4-dihydroxytetrahydro-2H-pyran-2-carboxylate (TCO-SiaOiPr)

The ethyl ester (TCO-SiaOEt) and the isopropyl ester (TCO-SiaOiPr) of TCO-Sia were prepared analogously to the procedure described for methyl ester 7 (point 5) but using EtOH or iPrOH as solvents in the reaction.

TCO-SiaOEt (Colorless Solid, 66%)

$^1$H NMR (MeOD, 400 MHz): δ=0.83-0.96 (m, 1H, H-6b-cyclooctene), 1.10-1.26 (m, 1H, H-7b cyclooctene), 1.33 (t, 3H, J=7.1 Hz, CH3-ethyl), 1.48-1.59 (m, 1H, H-5b-cyclooctene), 1.60-1.68 (m, OH, H-7a-cyclooctene), 1.68-1.76 (m, 1H, H-8b-cyclooctene), 1.78 (dd, OH, J=1.7, 3.4 Hz, H-3b), 1.83-1.97 (m, 1H, H-6a-cyclooctene), 1.96-2.12 (m, 5H, CH3CO, H-4b,5a,8a-cyclooctene), 2.23 (dd, 1H, J=4.9, 12.9 Hz, H-3a), 2.47 (d, 1H, J=10.5 Hz, H-4a-cyclooctene), 3.20 (dt, 1H, J=7.1, 14.1 Hz, H-9b), 3.42 (dd, 1H, J=1.5, 8.7 Hz, H-7), 3.59 (dt, 1H, J=4.0, 14.2 Hz, H-9a), 3.75 (dt, 1H, J=4.3, 8.3 Hz, H-8), 3.84 (t, 1H, J=10.2 Hz, H-5), 3.99-4.09 (m, 2H, H-4), 4.25 (qd, 2H, J=4.5, 7.1 Hz, H-1a,b-ethyl), 4.59 (s, 1H), 5.25-5.29 (m, 1H, 24 H-1-cyclooctene), 5.57 (dd, 1H, J=2.4, 16.4 Hz, H-2-cyclooctene), 5.82-5.93 (m, 1H, H-3-cyclooctene). $^{13}$C NMR (101 MHz, MeOD) δ=14.34 ($CH_2$—$CH_3$), 22.70 ($CH_3CO$); 25.20, ($CH_2$-7-cyclooctene); 30.09 ($CH_2$-6-cyclooctene); 36.79 ($CH_2$-4-cyclooctene); 37.03 ($CH_2$-5-cyclooctene); 40.67 ($CH_2$-3); 41.66 ($CH_2$-8-cyclooctene); 45.37 ($CH_2$-9); 54.32 (CH-5); 62.96 ($CH_2$—$CH_3$) 67.89 (CH-4); 71.04 (CH-8); 71.53 (CH-7); 72.05, 72.07 (CH-6); 75.30 (CH-1-cyclooctene); 96.60 (C-2); 132.62 (CH-3-cyclooctene); 132.83 (CH-2-cyclooctene); 159.06 (OCON); 171.32 ($CH_3CO$); 174.99 (C-1).

TCO-SiaOiPr (Colorless Solid, 32%)

$^1$H NMR (MeOD, 400 MHz): δ=0.89 (td, J=5.9, 13.5, 1H, H-6b-cyclooctene), 1.12-1.25 (m, 1H, H-7b cyclooctene), 1.23-1.38 (dd, 6H, $CH(CH_3)_2$), 1.45-1.56 (m, 1H, H-5b-cyclooctene), 1.66 (s, 1H, H-7a-cyclooctene), 1.75 (dddd, J=1.8, 3.5, 12.8, 14.8, 1H, H-8b-cyclooctene), 1.89 (td, J=5.4, 11.9, 2H, H-3b, H-6a-cyclooctene), 2.03 (s, 6H, CH3CO, H-4b,5a,8a-cyclooctene), 2.22 (dd, 1H, J=5.0, 12.9 Hz, H-3a), 2.47 (d, 1H, J=10.1 Hz, H-4a-cyclooctene), 3.20 (dt, 1H, J=7.4, 14.4, 1H, H-9b), 3.43 (dd, 1H, J=1.4, 8.3 Hz, H-7), 3.55-3.64 (m, 1H, H-9a), 3.75 (td, 1H, J=3.3, 7.8 Hz, H-8), 3.84 (t, 1H, J=10.3 Hz, H-5), 3.98-4.10 (m, 2H, H-4, H-6), 4.59 (s, 1H), 4.98-5.14 (m, 1H, $CH(CH_3)_2$), 5.27 (s, 1H, H-1-cyclooctene), 5.50-5.62 (m, 1H, H-2-cyclooctene), 5.87 (dd, 1H, J=11.1, 16.2, H-3-cyclooctene). $^{13}$C NMR (101 MHz, MeOD) δ=21.77, 21.83 ($CH(CH_3)_2$), 22.69 ($CH_3CO$); 25.21, ($CH_2$-7-cyclooctene); 30.10 ($CH_2$-6-cyclooctene); 36.80 ($CH_2$-4-cyclooctene); 37.03 ($CH_2$-5-cyclooctene); 40.65 ($CH_2$-3); 41.66 ($CH_2$-8-cyclooctene); 45.34 ($CH_2$-9); 54.34 (CH-5); 67.95 (CH-4); 70.99 ($CH(CH_3)_2$, 71.26 (CH-8); 71.61 (CH-7); 72.12 (CH-6); 75.30 (CH-1-cyclooctene); 96.56 (C-2); 132.63 (CH-3-cyclooctene); 132.85 (CH-2-cyclooctene); 159.05 (OCON); 171.90 ($CH_3CO$); 175.02 (C-1).

II. Synthesis of Tetrazine Conjugates

Example 3: Preparation of (S)—N[1]-(18-methyl-15-oxo-16-(4-(4-sulfamoylphenyl)-1H-1,2,3-triazol-1-yl)-4,7,10-trioxa-14-azanonadecyl)-N[4]-(6-(6-(pyridin-2-yl)-1,2,4,5-tetrazin-3-yl)pyridin-3-yl)succinamide (sulfonamide-PEG3-diPyTz Conjugate)

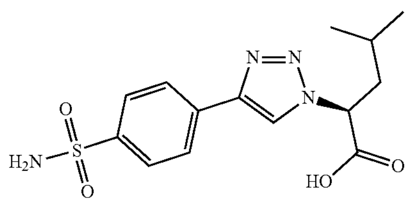

Sulfonamide COOH

+

-continued

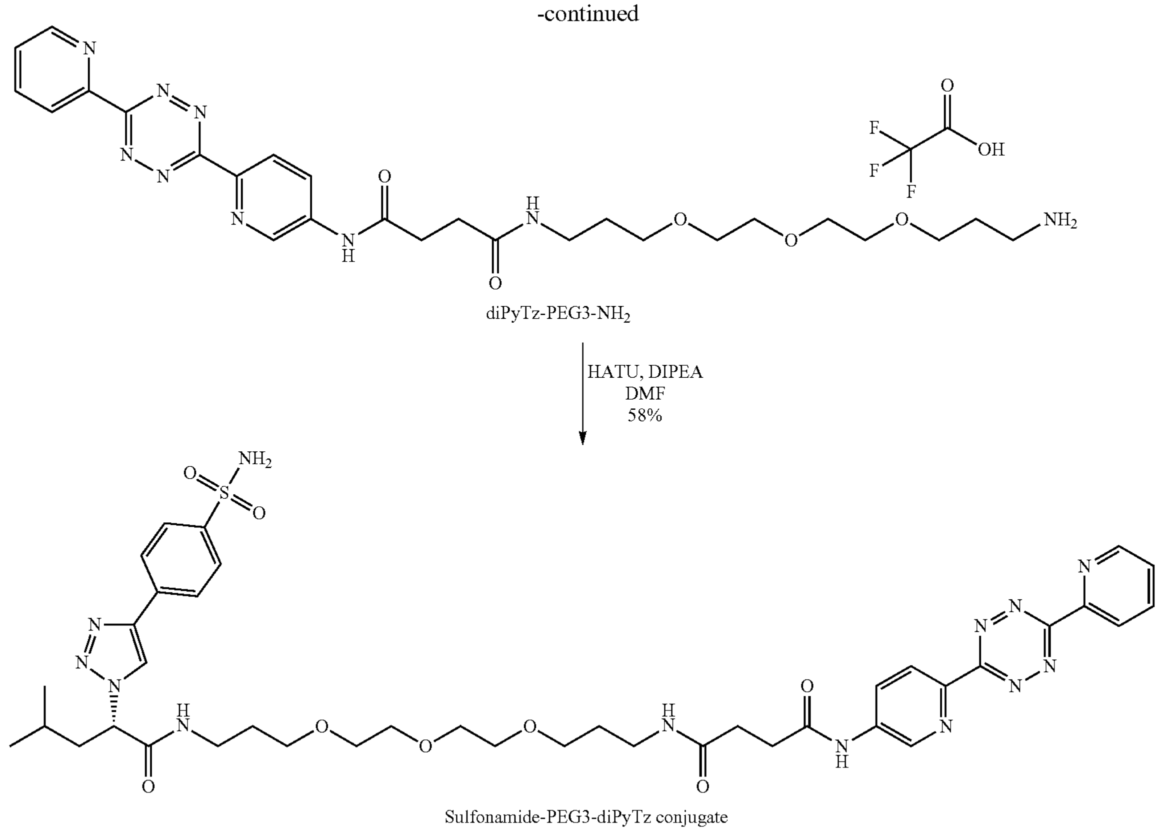

diPyTz-PEG3-$NH_2$

Sulfonamide-PEG3-diPyTz conjugate

1. The starting sulfonamide carboxylic acid (Sulfonamide COOH) (prepared according to: Mocharla et al. Angewandte Chemie International Edition 44 (1): 116, 2005) (6 mg) and 1-[Bis(dimethylamino)methylene]-1H-1,2,3-triazolo[4,5-b]pyridinium 3-oxid hexafluorophosphate (HATU, 7.4 mg) were dissolved in dry DMF (0.5 mL), and the solution was cooled down in an ice/water bath. Dipyridyl tetrazine-PEG3-amine (diPyTz-PEG3-$NH_2$) (prepared according to: Siegl et al. Chemistry a European Journal, 24 (10): 2426, 2018) dissolved in dry DMF (0.25 mL) was then added dropwise to the reagents. The vial with diPyTz-PEG3-$NH_2$ was washed with additional dry DMF (0.25 mL), and the solution was added to the reagents. Finally, diisopropylethylamine (15 μL) was added to the reaction mixture. After one hour water (1 mL) was added to quench the reaction, and the solvent was evaporated under reduced pressure. The residue was purified by RP C18 flash column chromatography (using a gradient of $CH_3CN$ in water, both containing 0.05% HCOOH) to yield the product sulfonamide-PEG3-diPyTz conjugate as a reddish solid after lyophilization (10.3 mg). The product was characterized by RP HPLC-MS (FIG. 1).

Example 5: Preparation of Biotin-PEG3-diPy-Tz Conjugate

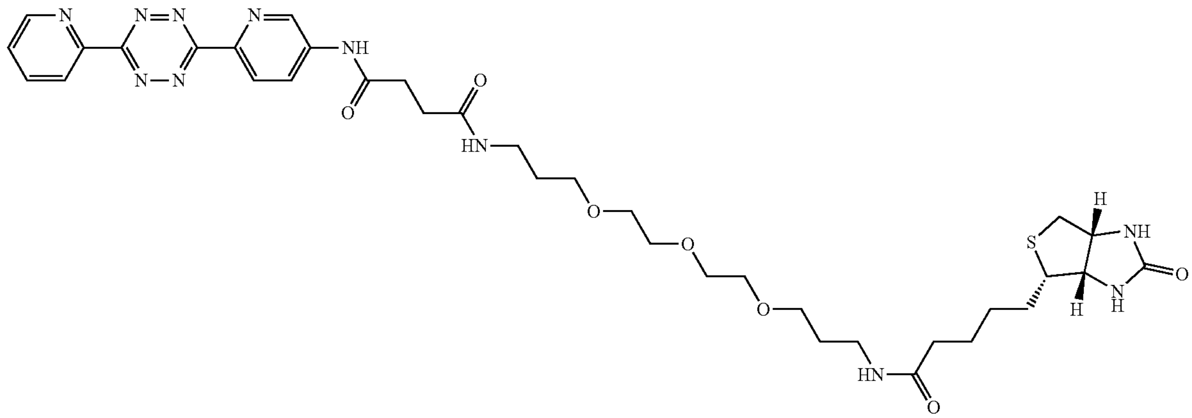 [SMILES: O=C(CCCC[C@@H]1SC[C@@H]2NC(=O)N[C@@H]21)NCCCOCCOCCOCCCNC(=O)CCC(=O)Nc1ccc(-c2nnc(-c3ccccn3)nn2)nc1]

To a solution of 4-oxo-4-((6-(6-(pyridin-2-yl)-1,2,4,5-tetrazin-3-yl)pyridin-3-yl)amino)butanoic acid (300 mg, 0.854 mmol) and N-Boc-4,7,10-trioxa-1,13-tridecanediamine (342 mg, 1.07 mmol) in anhydrous DMF (10 mL) was under argon at 0° C. added HATU (406 mg, 1.07 mmol) followed by DIPEA (446 μL, 0.0793 mmol). The solution was stirred under argon at room temperature for 1 h, concentrated in vacuo and purified by silica gel column chromatography (DCM/MeOH 10:1) to provide the Boc-protected intermediate as colorless oil (530 mg, 80%) which was used directly in the next step.

Deprotection of the Boc-protected intermediate (150 mg, 0.229 mmol) was carried out in DCM (5 mL) by adding dropwise TFA (0.25 mL) and stirring the mixture at room temperature for 1 h. The deprotected intermediate was concentrated in vacuo, dried under high vacuum and used in the next step.

The deprotected intermediate was dissolved together with biotin (56.1 mg, 0.229 mmol) in anhydrous DMF (2.5 mL). Then HATU (96.0 mg, 0.252 mmol) and DIPEA (200 μL, 1.15 mmol) were added under argon at 5° C. and the solution was stirred at room temperature for 20 h. MeOH was added and the mixture was concentrated in vacuo and dried under high vacuum. The crude product was purified by silica gel column chromatography (DCM/MeOH 5:1). Remaining impurities were removed by reverse phase flash column chromatography ($CH_3CN/H_2O$ mixture) to provide Biotin-PEG3-diPy-Tz conjugate as red semisolid (85 mg, 45%).

$^1H$ NMR (401 MHz, DMSO-$d_6$): δ 10.63 (s, 1H), 9.05 (dd, J=2.6, 0.7 Hz, 1H), 8.93 (ddd, J=4.7, 1.8, 0.9 Hz, 1H), 8.62 (dd, J=8.7, 0.6 Hz, 1H), 8.59 (dt, J=8.0, 1.1 Hz, 1H), 8.41 (dd, J=8.7, 2.5 Hz, 1H), 8.15 (td, J=7.8, 1.8 Hz, 1H), 7.90 (t, J=5.6 Hz, 1H), 7.75-7.69 (m, 2H), 6.42-6.35 (m, 2H), 4.30 (ddt, J=7.6, 5.2, 1.1 Hz, 1H), 4.12 (ddd, J=7.5, 4.4, 2.0 Hz, 1H), 3.52-3.45 (m, 8H), 3.39 (dt, J=8.6, 6.4 Hz, 4H), 3.12-3.03 (m, 5H), 2.81 (dd, J=12.4, 5.1 Hz, 1H), 2.67 (t, J=7.0 Hz, 2H), 2.57 (d, J=12.4 Hz, 1H), 2.46 (t, J=7.0 Hz, 2H), 2.04 (t, J=7.4 Hz, 2H), 1.64-1.57 (m, 4H), 1.52-1.42 (m, 2H), 1.35-1.22 (m, 4H).

$^{13}C$ NMR (101 MHz, DMSO-$d_6$): δ 171.9, 171.8, 170.9, 163.0, 162.8, 162.7, 150.6, 150.2, 143.7, 141.2, 138.6, 137.8, 126.6, 126.0, 124.9, 124.2, 69.8, 69.5, 68.10, 68.06, 61.1, 59.2, 55.4, 40.1, 35.9, 35.7, 35.2, 31.7, 30.0, 29.41, 29.39, 28.2, 28.0, 25.3.

HRMS (ESI): m/z calcd. for $C_{36}H_{50}N_{11}O_7S$ $[MH]^+$ 780.3610, found 780.3613 and m/z calcd. for $C_{36}H_{49}NaN_{11}O_7S$ $[M+Na]^+$802.3429, found 802.3432.

Example 6: Preparation of FITC-MeTz Conjugate

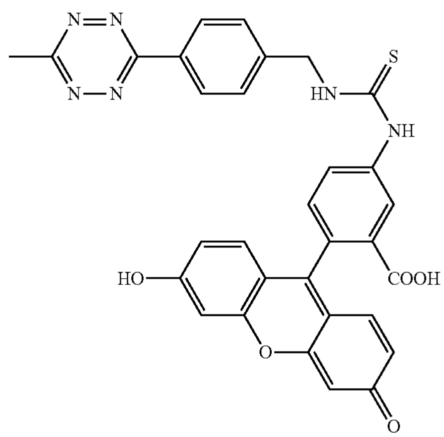 [SMILES: Cc1nnc(-c2ccc(CNC(=S)Nc3ccc(-c4c5ccc(=O)cc-5oc5cc(O)ccc45)c(C(=O)O)c3)cc2)nn1]

To a solution of 6-methyl-3-benzyl-tetrazine-amine (TFA salt, 10 mg, 0.0317 mmol) in anhydrous DMF (2.5 mL) was added DIPEA (13.8 μL, 0.0793 mmol) followed by fluorescein-5-isothiocyanate (12.4 mg, 0.0317 mmol). The reaction mixture was stirred in the dark at room temperature until the starting materials disappeared (TLC in DCM/MeOH 9:1) and then concentrated in vacuo. The crude product was purified by silica gel column chromatography (EtOAc→EtOAc/MeOH 20:1) to provide FITC-MeTz conjugate as red viscous oil which was re-dissolved in $CH_3CN/H_2O$ and lyophilized to give the title compound as red-orange solid (16 mg, 85%).

The formation of the product was verified by HPLC-MS and HRMS.

HRMS (ESI): m/z calcd. for $C_{31}H_{23}N_6O_5S$ $[MH]^+$ 591.1445, found 591.1446.

Example 7: Preparation of BDP-MeTz Conjugate

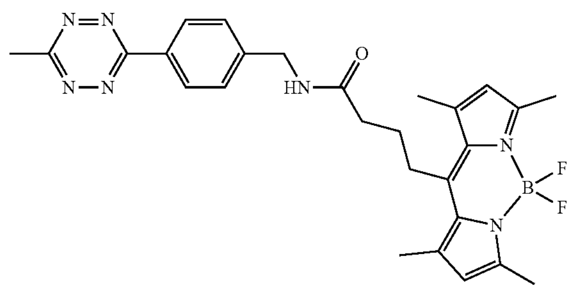

To a solution of 6-methyl-3-benzyl-tetrazine-amine (TFA salt, 22 mg, 0.070 mmol) in anhydrous DMF (2 mL) was added bodipy NHS active ester (15 mg, 0,035 mmol, prepared according to Journal of Organic Chemistry 2006, 71, 1718) and DIPEA (61 μL, 0.351 mmol, 5 equiv.) at 0° C. The reaction mixture was stirred in the dark at room temperature until the starting materials disappeared (ca. 2 hours, verified by TLC in AcOEt/Hex/DCM 3:1:1). The reaction mixture was diluted with AcOEt (50 mL), washed with $H_2O$ and brine. The organic phase was dried over $MgSO_4$ and concentrated in vacuo. The crude product was purified by silica gel column chromatography (AcOEt/Hex/DCM 3:1:1) to provide BDP-MeTz conjugate as orange solid (10 mg, 56%).

HRMS (ESI): m/z calcd. for $C_{27}H_{30}N_7OBF_2$ $[M+Na]^+$ 540.2465, found 540.2466.

Example 8: Preparation of 7-(Azetidin-1-yl)-4-methyl-3-(5-(6-phenyl-1,2,4,5-tetrazin-3-yl)pyridin-3-yl)-2H-chromen-2-one conjugate (Coumarin-Tz1)

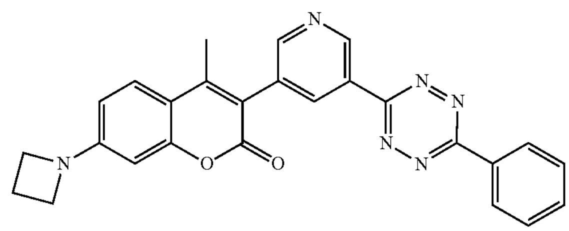 [SMILES: Cc1c(-c2cncc(-c3nnc(-c4ccccc4)nn3)c2)c(=O)oc2cc(N3CCC3)ccc12]

This compound was prepared following literature procedure (Galeta et al. Chemistry A European Journal 26(44), 9945, 2020).

$^1$H NMR ($CDCl_3$): δ 9.83 (d, J=2.1, 1H), 8.90 (t, J=2.1, 1H), 8.81 (d, J=2.1, 1H), 8.69-8.65 (m, 2H), 7.68-7.60 (m, 3H), 7.51 (d, J=8.8, 1H), 6.37 (dd, J=8.8, 2.3, 1H), 6.28 (d, J=2.3, 1H), 4.05 (t, J=7.4, 4H), 2.52-2.43 (m, 2H), 2.35 (s, 3H).

$^{13}$C NMR ($CDCl_3$): δ 164.5 (C), 163.1 (C), 161.6 (C), 155.2 (C), 154.9 (CH), 154.2 (C), 150.3 (C), 148.2 (CH), 137.4 (CH), 133.2 (CH), 132.1 (C), 131.7 (C), 129.6 (2×CH), 128.4 (2×CH), 127.7 (C), 126.4 (CH), 117.2 (C), 110.3 (C), 108.2 (CH), 96.9 (CH), 51.8 (2×$CH_2$), 16.8 ($CH_3$), 16.6 ($CH_2$).

HRMS (ESI): m/z calcd. for $C_{26}H_{21}N_6O_2$ $[MH]^+$ 449.1721, found: 449.1718.

Example 9: Preparation of 7-(Azetidin-1-yl)-4-methyl-3-(5-(6-pyrimidin-2-yl)-1,2,4,5-tetrazin-3-yl)pyridin-3-yl)-2H-chromen-2-one (Coumarin-Tz2)

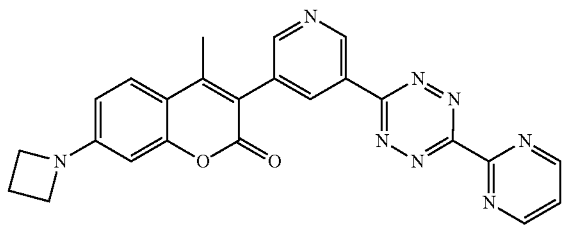 [SMILES: Cc1c(-c2cncc(-c3nnc(-c4ncccn4)nn3)c2)c(=O)oc2cc(N3CCC3)ccc12]

This compound was prepared following literature procedure (Galeta et al. Chemistry A European Journal 26(44): 9945, 2020).

$^1$H NMR ($CDCl_3$): δ 9.90 (d, J=2.1, 1H), 9.14 (d, J=4.9, 2H), 8.96 (t, J=2.1, 1H), 8.84 (d, J=2.1, 1 H), 7.60 (t, J=4.9, 1H), 7.50 (d, J=8.7, 1H), 6.36 (dd, J=8.7, 2.3, 1H), 6.26 (d, J=2.3, 1H), 4.04 (t, J=7.4, 4H), 2.51-2.42 (m, 2H), 2.34 (s, 3H).

$^{13}$C NMR ($CDCl_3$): δ 163.8 (C), 163.6 (C), 161.5 (C), 159.5 (C), 158.6 (2×CH), 155.5 (CH), 155.2 (C), 154.2 (C), 150.4 (C), 149.0 (CH), 138.1 (CH), 132.2 (C), 127.2 (C), 126.4 (CH), 122.8 (CH), 117.0 (C), 110.2 (C), 108.2 (CH), 96.8 (CH), 51.8 (2×$CH_2$), 16.8 ($CH_3$), 16.6 ($CH_2$).

Example 10: 7-(Azetidin-1-yl)-3-(3-(6-(2-hydroxyethyl)-1,2,4,5-tetrazin-3-yl)phenyl)-4-methyl-2H-chromen-2-one (Coumarin-Tz3)

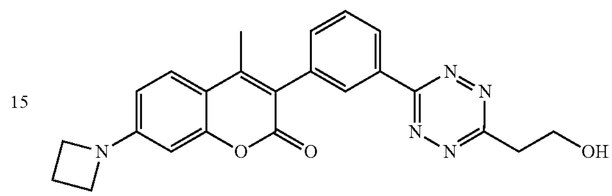

This compound was prepared following literature procedure (Galeta et al. Chemistry A European Journal 26(44): 9945, 2020).

$^1$H NMR ($CDCl_3$): δ 8.59-8.55 (m, 1H), 8.52-8.50 (m, 1H), 7.68-7.63 (m, 1H), 7.60-7.56 (m, 1H), 7.47 (d, J=8.7, 1H), 6.34 (dd, J=8.7, 2.3, 1H), 6.26 (d, J=2.3, 1H), 4.27 (t, J=5.9, 2H), 4.01 (t, J=7.3, 4H), 3.60 (t, J=5.9, 2H), 2.77 (bs, 1H), 2.49-2.40 (m, 2H), 2.28 (s, 3H).

$^{13}$C NMR ($CDCl_3$): δ 168.4 (C), 164.5 (C), 161.8 (C), 154.9 (C), 153.9 (C), 149.3 (C), 136.7 (C), 135.1 (CH), 131.8 (C), 130.3 (CH), 129.5 (CH), 127.4 (CH), 126.2 (CH), 120.7 (C), 110.6 (C), 108.1 (CH), 96.9 (CH), 60.2 ($CH_2$), 51.9 (2×$CH_2$), 37.7 ($CH_2$), 16.7 ($CH_3$), 16.6 ($CH_2$).

HRMS (ESI): m/z calcd. for $C_{23}H_{22}N_5O_3$ $[MH]^+$ 416.1717, found: 416.1716.

Example 11: Preparation of MeTz-PEG3-PEG3-biotin-PEG3-DBCO Conjugate

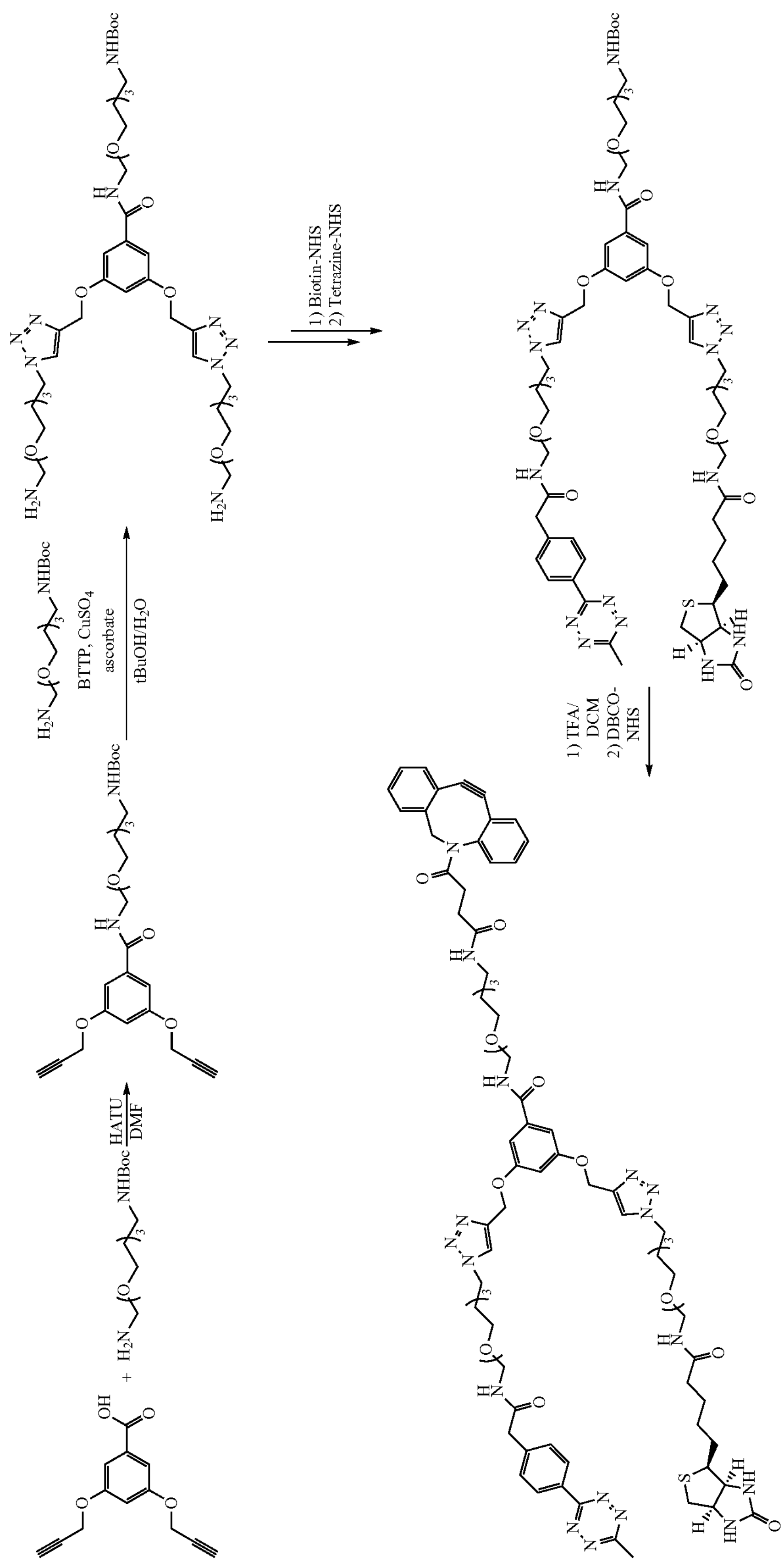
HATU
DMF
BTTP, CuSO4
ascorbate
tBuOH/H2O
1) Biotin-NHS
2) Tetrazine-NHS
1) TFA/
DCM
2) DBCO-
NHS 3,5-bis(prop-2-yn-1-yloxy)benzoic acid (345 mg, 1.5 mmol) and the N-Boc protected diamine (1.2 equiv.) were dissolved in dry DMF and the solution was cooled down in ice/water bath. HATU (1.2 equiv.) and DIPEA (3 equiv.) were added to the solution which was then stirred at room temperature for 1 hour. The reaction mixture was diluted with AcOEt and the organic phase was washed with water and brine. The organic phase was dried over $Na_2SO_4$, the solvent was evaporated under reduced pressure and the residue was purified by silica gel column chromatography (gradient of MeOH in DCM from 2 to 4%) to give the desired compound as dense oily solid (763 mg). This intermediate (50 mg) was combined with azido-PEG3-amine (43 mg) and the mixture was dissolved in mixture of tert-butanol/water=2/3 (1 mL). A premixed solution of BTTP ligand (4 mg) and $CuSO_4.5H_2O$ (1.8 mg) in water (100 μL) was combined with a solution of sodium ascorbate (3.7 mg) in water (100 μL) and this colorless solution was added to the solution of reactants. Progress of the reaction was followed by LC-MS. After one hour the solvent was removed under reduced pressure and the residue was purified by RP C18 flash column chromatography (using a gradient of $CH_3CN$ in water, both containing 0.05% HCOOH) to yield the bis-amino N-Boc-protected intermediate (50 mg). To solution of this intermediate (45 mg) in dry DMF (1.5 mL) and cooled down in ice/water bath was added biotin-NHS ester (from Merck, 16 mg) dissolved in dry DMF (0.5 mL) followed by DIPEA (10 μL). The reaction was stirred at room temperature for 30 min after which, another portion of DIPEA (10 μL) was added followed by the addition of MeTz-NHS ester (from Merck, 15.2 mg). After stirring the reaction for 30 minutes, the solvent was removed under reduced pressure and the residue was purified by RP C18 flash column chromatography (using a gradient of $CH_3CN$ in water, both containing 0.05% HCOOH) to yield the MeTz-PEG3-PEG3-biotin-PEG3-N-Boc amine intermediate (25 mg). To this intermediate (25 mg) dissolved in DCM (2 mL) was added TFA (0.2 mL) and the reaction was stirred at room temperature for 1 hour. The reaction mixture was diluted with DCM (10 mL) and the solvent was removed under reduced pressure and the residue was dried using high vacuum. To this compound (25 mg) dissolved in dry DMF (1.5 mL) cooled down in ice/water bath was added HBTU (7 mg) and DBCO acid (from Conjuprobe, 5.6 mg). The resulting solution was stirred at room temperature under argon atmosphere overnight. The solvent was removed under reduced pressure and the residue was purified by RP C18 flash column chromatography (using a gradient of $CH_3CN$ in water, both containing 0.05% HCOOH) to yield the MeTz-PEG3-PEG3-biotin-PEG3-DBCO as red solid after lyophilization (19 mg). The product was characterized by LC-MS.

HRMS (ESI): m/z calcd. for $C_{79}H_{103}N_{17}O_{17}NaS$ $[M+Na]^+$1616.73308, found 1616.73264.

Example 12: Preparation of NRP-NBD-PEG9-HTz Peptide Conjugate

The following Neuropilin (NRP)-binding peptide (RPARPAR) (prepared according to: Teesalu et al. Proceedings of the National Academy of Sciences, 106 (38): 16157, 2009) with additional Lysine-Alanine linker was assembled using standard Fmoc solid-phase peptide synthesis on HypoGel-4-Hydroxymethylbenzoylamide resin.

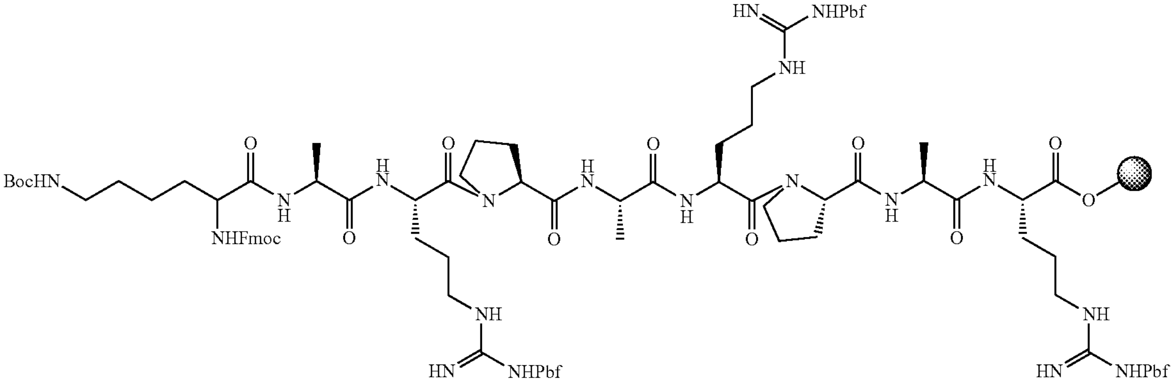

Figure 2:
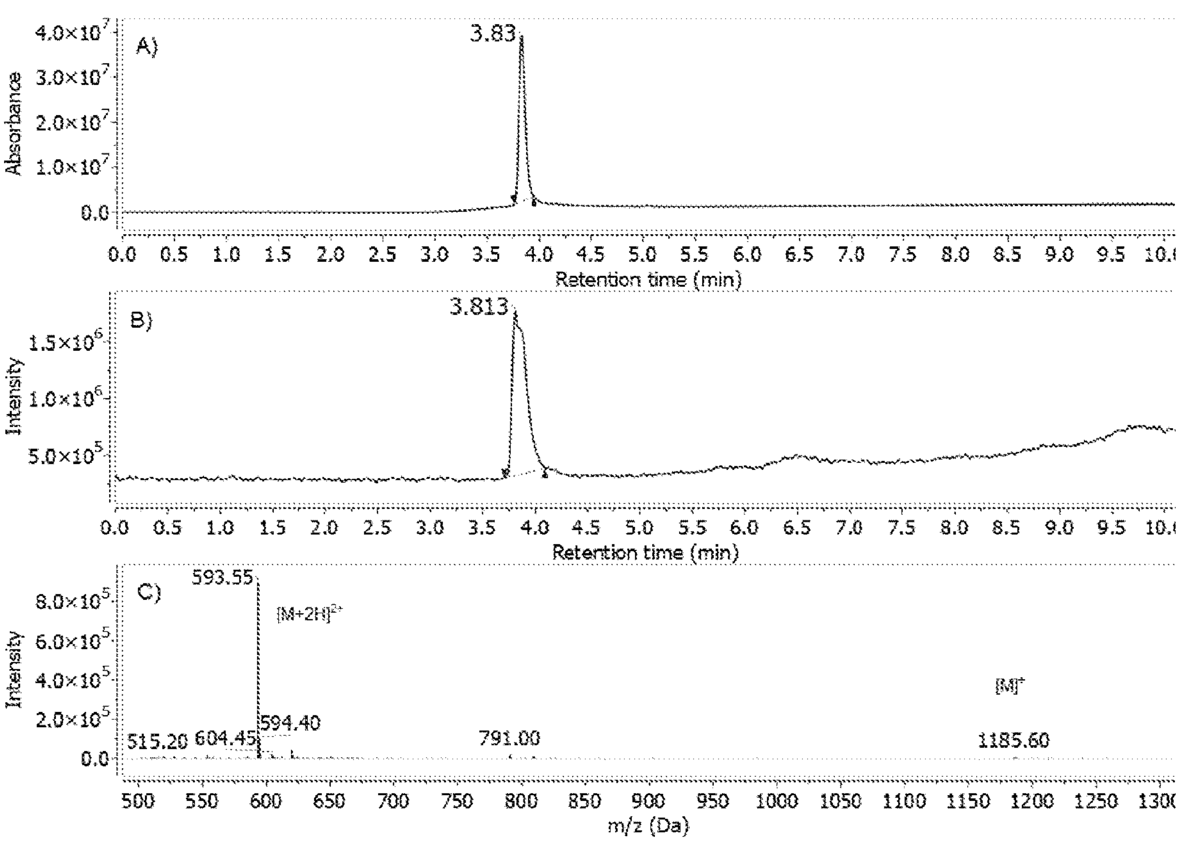
FIG. 2: HPLC-MS analysis of NRP-NBD peptide. A) PDA total absorbance chromatogram, B) TIC (total ion count) chromatogram, C) extracted m/z from signal at 3.81 min.

NRP peptide 1. 40 mg of the resin-bound NRP peptide (ca. 0.0136 mmol) was soaked with DMF and washed with DMF. The Fmoc group was deprotected by incubation of the NRP resin-bound peptide with 20% piperidine in DMF (5 mL, 2×20 min), and the resin was washed with DMF, DCM and DMF.
2. This step was performed to attach the fluorescent dye (NBD) onto the NRP peptide to detect its presence after the modification of the cells. The Fmoc-deprotected NRP peptide on the resin from the previous step was incubated with 4-Chloro-7-nitrobenzofurazan (NBD-Cl) (7 mg) and diisopropylethylamine (DIPEA, 6 μL) in DMF (1.5 mL) for 60 minutes. The resin was washed with DMF, DCM and DMF, and this step was repeated two more times using the same amounts of reagents and solvents. The resin was then washed with DMF, DCM, DMF, DCM, and was vacuum dried.
3. The resin-bound peptide was then incubated with a mixture of trifluoroacetic acid/triisopropylsilane/water=90/2/8 (1.5 mL) for one hour. The resin was washed with DCM and the procedure was repeated two more times.
4. One half of the resin-bound NRP peptide from the previous step was soaked in a dioxane/water mixture and briefly vacuum dried. The resin-bound peptide was then incubated in dioxane (100 μL), water (500 μL) and 1 M NaOH solution in water (60 μL) for 20 min. The resin was spun down in a plastic vial and the liquid phase was neutralized with 1M HCl in water (60 μL), then the liquid was pipetted off. This cleavage procedure was repeated once again. The combined cleavage liquids were diluted to ca. 5 mL with water containing 0.1% TFA, filtered, and the residue was purified by C18 RP HPLC. Fractions containing the peptide were combined to obtain the desired NRP-NBD-peptide after lyophilization as an orange solid (26 mg). The product was characterized by RP HPLC-MS (FIG. 2).

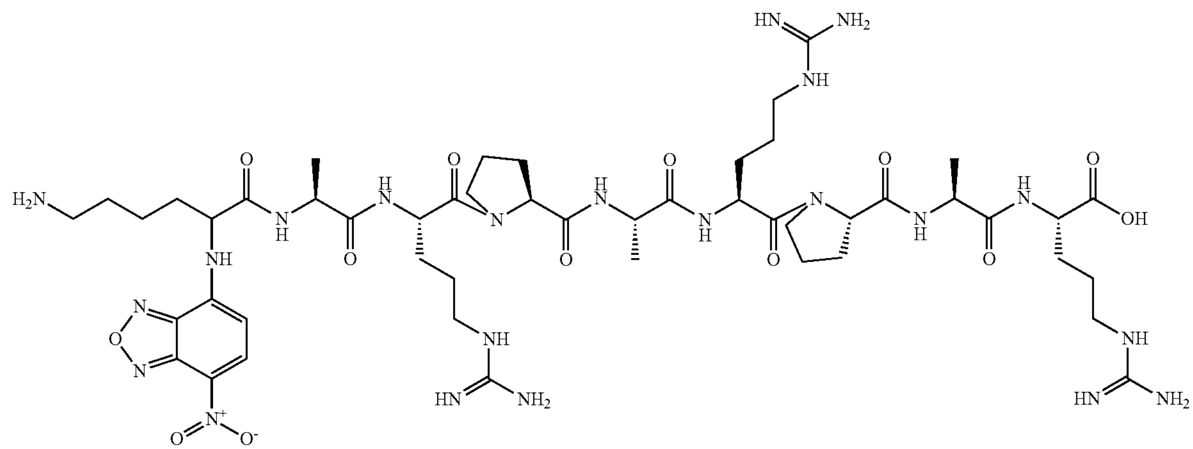

NRP-NBD peptide

Figure 3:
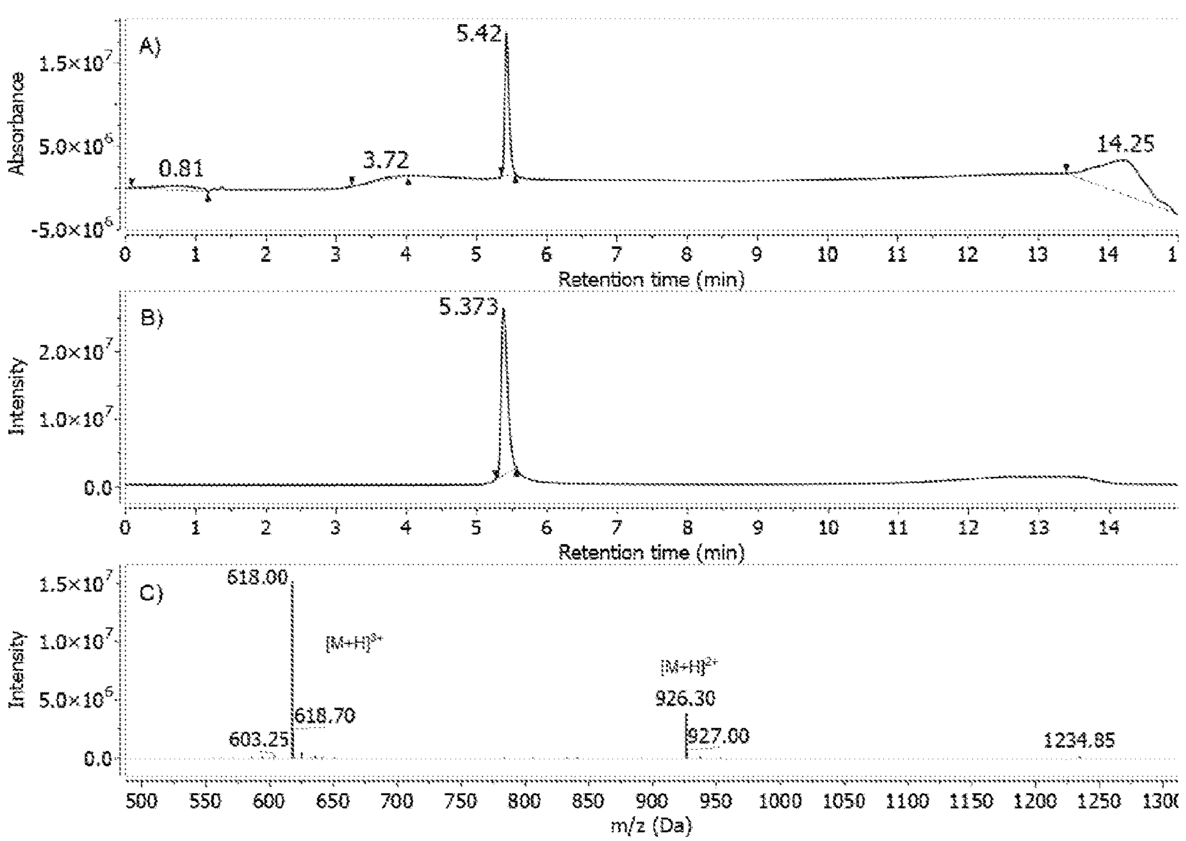
FIG. 3: HPLC-MS analysis of NRP-NBD-PEG9-HTz peptide conjugate. A) PDA total absorbance chromatogram, B) TIC (total ion count) chromatogram, C) extracted m/z from signal at 5.37 min.

5. The NRP-NBD peptide (8.5 mg) from the previous step was dissolved in HEPES buffer (pH=8.3, 50 mM), and HTz-PEG9-NHS ester (4 mg) (from Conju-Probe, CP-6026) dissolved in DMSO was added to the peptide solution. After 4 hours, the reaction mixture was diluted with water containing 0.05% HCOOH, the liquid was filtered through a syringe filter (0.2 μm PTFE), and the residue was purified by C18 RP HPLC to obtain the NRP-NBD-PEG9-HTz peptide conjugate as an orange solid after lyophilization (6 mg). The product was characterized by RP HPLC-MS (FIG. 3).

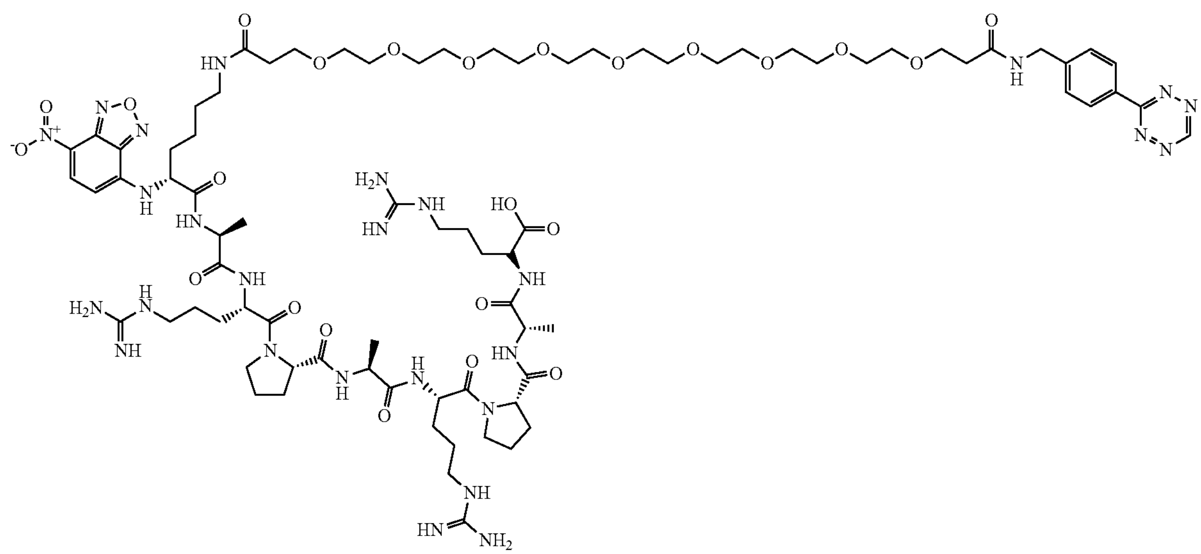

NRP-NBD-PEG9-HTz peptide conjugate

Example 13: Preparation of FLAG-MeTz Peptide Conjugate

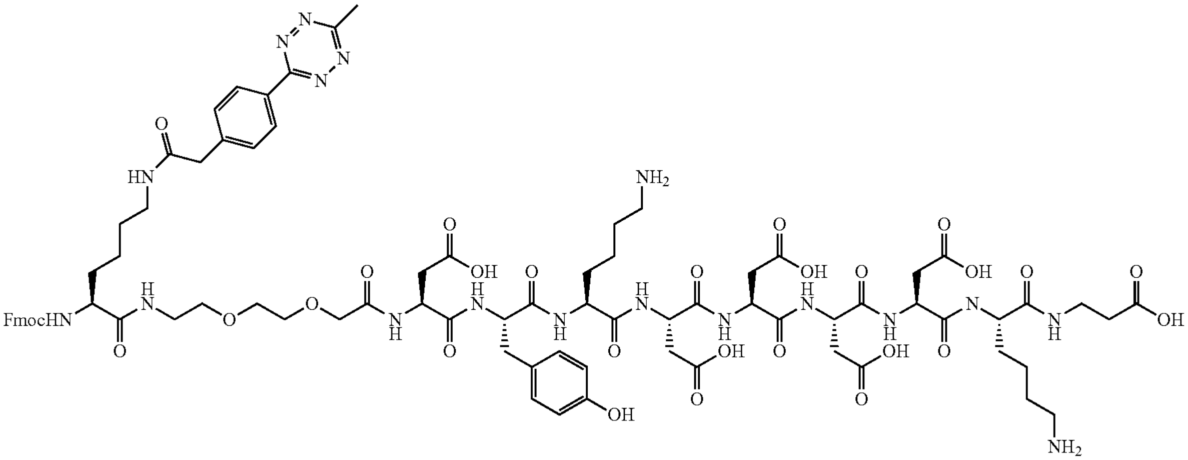

This conjugate was prepared as previously described in La-Venia et al. Chemistry A European Journal 27(54), 13632, 2021.

Example 14: Preparation of Cy3 Labeled Duplex Oligonucleotide Tetrazine Conjugate (Cy3-Oligonucleotide-HTz)

0.176 μmol of synthetic commercial DNA oligonucleotide modified at the 3' end with Amine-C7 (sequence 5'-TT-GAATAAGCTGGTAAT-3'-[AmC7], SEQ ID NO. 1) was dissolved in 200 μL of 20 mM HEPES pH 8.3, and combined with 17.6 μL of 50 mM HTz-peg5-NHS ester (Conju-Probe, cat. no. CP-6025, 5× molar excess). The reaction was incubated for 4 hours, after which time another portion of 50 mM tetrazine (5× molar excess) was added and the reaction was incubated for another 12 hours. Unreacted tetrazine was removed from the reaction by ethanol precipitation. Briefly, the oligonucleotide was precipitated by adding 1 mL of EtOH/3M sodium acetate (9:1 V/V) solution to the conjugation reaction. After vigorous vortexing, the tube was spun down for 20 min at 25000×g/4° C. The precipitated pellet was washed with 500 μL of cold 70% EtOH (−20° C.), then centrifuged for 20 min at 25000×g/4° C. The washing step was repeated twice. The pellet was then briefly dried in a speedvac and resuspended in $H_2O$. The presence of tetrazine modification on the oligonucleotide was confirmed by mass spectrometry. Tz-modified oligonucleotide from the previous step was combined with an equal amount of a synthetic commercial complementary oligonucleotide modified at its 5' end with Cy-3 dye. (sequence [Cy3]-5'-ATACCAGCTT-ATTCAATT-3', SEQ ID NO. 2). The reaction was heated to 50° C. for 5 minutes and then cooled down slowly to room temperature to obtain the duplex Cy3-Oligonucleotide-HTz.

Example 15: Preparation of Trastuzumab-HTz Conjugate

An aliquot of 100 μL (3.44 nmol) of the humanized Anti-Human HER2, Antibody (Trastuzumab, Med Chem Express, cat. No. HY-P9907, 5 mg/mL, approximately 34.4 μM) was buffer-exchanged using a Zeba desalting spin column into 50 mM HEPES, pH 8.3. A 5× molar excess of HTz-Peg5-NHS ester (CP-6025, Conju-Probe) was added to this amount of antibody, and the mixture was incubated for 30 min, after which time another aliquot of HTz-Peg5-NHS ester (5× molar excess) was added, and the mixture was incubated for a further 30 minutes. After this time, unconjugated tetrazine was removed by passing the reaction mixture through a pre-equilibrated (PBS) Zeba desalting column to obtain Trastuzumab-HTz conjugate.

Example 16: Preparation of Cetuximab-HTz Conjugate

An aliquot of 100 μL (3.44 nmol) of the humanized Anti-Human EGFR, Antibody (Cetuximab, Med Chem Express, cat. No. HY-P9905, 5 mg/mL, approximately 34.4 μM) was buffer-exchanged using a Zeba desalting spin column into 50 mM HEPES, pH 8.3. A 5× molar excess of HTz-PEG5-NHS ester (CP-6025, Conju-Probe) was added to this amount of antibody, and the mixture was incubated for 30 min, after which time another aliquot of HTz-PEG5-NHS ester (5× molar excess) was added, and the mixture was incubated for a further 30 minutes. After this time, unconjugated tetrazine was removed by passing the reaction mixture through a pre-equilibrated (PBS) Zeba desalting column to obtain Cetuximab-PEG5-HTz conjugate.

Example 17: Preparation of Phycoerythrin-PEG-Tz Conjugates

50 μL of R-phycoerythrin (precipitate—4 mg/mL solution in 60% saturated ammonium sulfate, 50 mM potassium phosphate, pH 7.0) was pelleted at 25 000 g/10 min. Supernatant was removed and the pellet was resuspended in 100 μL of PBS and buffer-exchanged into 150 mM NaCl, 50 mM HEPES pH8.3 using Zeba desalting columns (Thermo). Active ester of methyltetrazine-PEG4-NHS ester (Click Chemistry Tools, 1069-1) was added to the protein in 5× molar excess. After one hour of incubation, another aliquot of methyltetrazine-PEG4-NHS ester (5× molar excess) was added and the reaction was incubated for another hour. After this time unreacted tetrazine was removed using Zeba desalting column giving Phycoerythrin-PEG4-MeTz conjugate.

The same procedure using HTz-PEG5-NHS ester (Conjuprobe, CP-6025-25 MG) and HTz-PEG9-NHS ester (Conjuprobe, CP-6026) was used for preparation of Phycoerythrin-PEG5-HTz and Phycoerythrin-PEG9-HTz conjugates.

III. Incorporation of TCO-Sia into Cells and Labeling of Cell Surfaces with Tetrazine Conjugates

Cells and Cultivation Conditions

All cell lines were obtained from ATCC and cultivated in a humidified atmosphere incubator at 37° C./5% $CO_2$. Human peripheral blood mononuclear cells (PBMCs) were freshly isolated from the blood of a healthy human donor. All cultivation media were supplemented with antibiotics (Pen-Strep, Sigma, cat. No. P4333). U20S and MDCK cells were incubated in high-glucose DMEM medium (Biowest, Cat. No. L0103) supplemented with 10% fetal bovine serum (Thermo, cat. No. 10270106). Raji and Jurkat cells were cultivated in RPMI 1640 medium (Biowest, Cat. No. L0492, Dutch Modification, with 1 g/L Sodium Bicarbonate and 20 mM HEPES) containing 10% FBS and 1× concentrated Glutamax (Thermo, Cat. No. 35050061). THP-1 cells were cultivated in RPMI 1640 (Dutch modification) containing 10% Ultra low Endotoxin FBS (Biosera, Cat. No. FB-1001) and 1× concentrated Glutamax. NK-92MI cells were cultivated in RPMI 1640 (Dutch modification) containing 12.5% FBS and 12.5% Horse serum (Thermo, cat. No. 26050088) and 1× concentrated Glutamax. For some incubations and microscopy, cells were kept in Leibowitz's L15 medium without phenol red (Thermo, Cat. No. 21083027) containing 10% FBS and antibiotics.

Microscopy and Flow Cytometry

Images of live U20S cells were obtained using a Zeiss LSM780 AxioObserver, equipped with a C-Apochromat 40×/1.20 W Korr FCS M27 objective. The excitation wavelength for Cy3 was 561 nm, emission was collected in the 569-630 nm window. The image was exported in grayscale and inverted in ImageJ software. Flow cytometric measurements (FACS) were performed in a BD LSR Fortessa flow cytometer with the following setup, Cy3-excitatory laser 561 nm, mirror 600LP, filter 610/20 nm; NBD-excitatory laser 488 nm, mirror 505LP, filter 530/30 nm. The fluorescence of more than 5000 singlets was recorded each time, the raw data were processed using the software FlowJo (FlowJo, LLC).

Example 18: Incorporation of TCO-Sia and Test of Cell Viability

Figure 4:
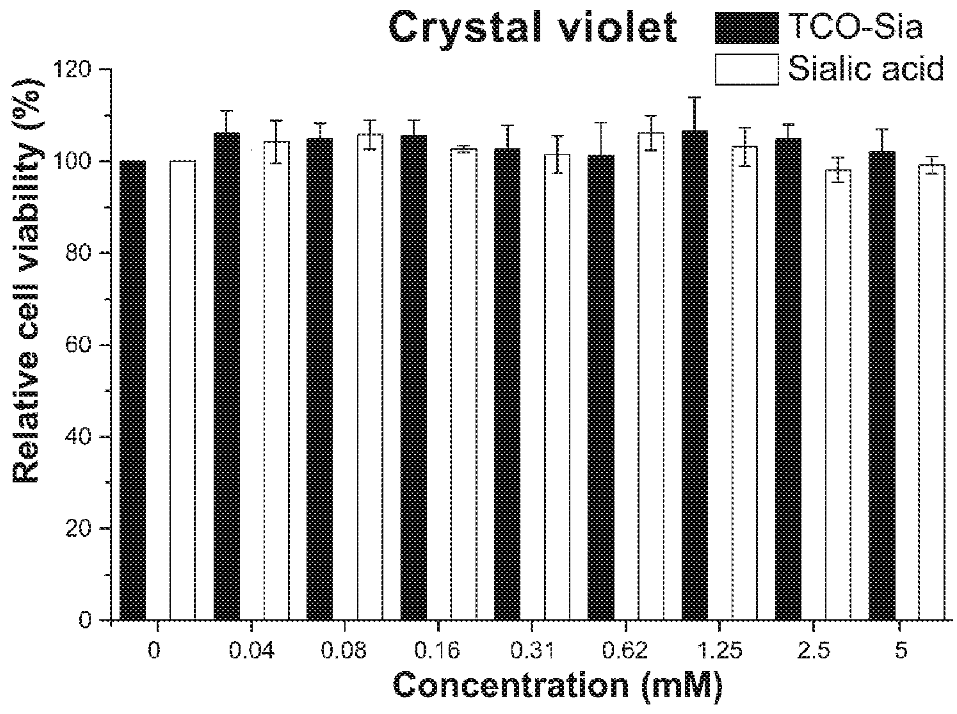
FIG. 4: Cell viability of U2OS cells incubated with the indicated concentrations of carbohydrates assessed by crystal violet and resazurin cell viability assay.
Figure 4:
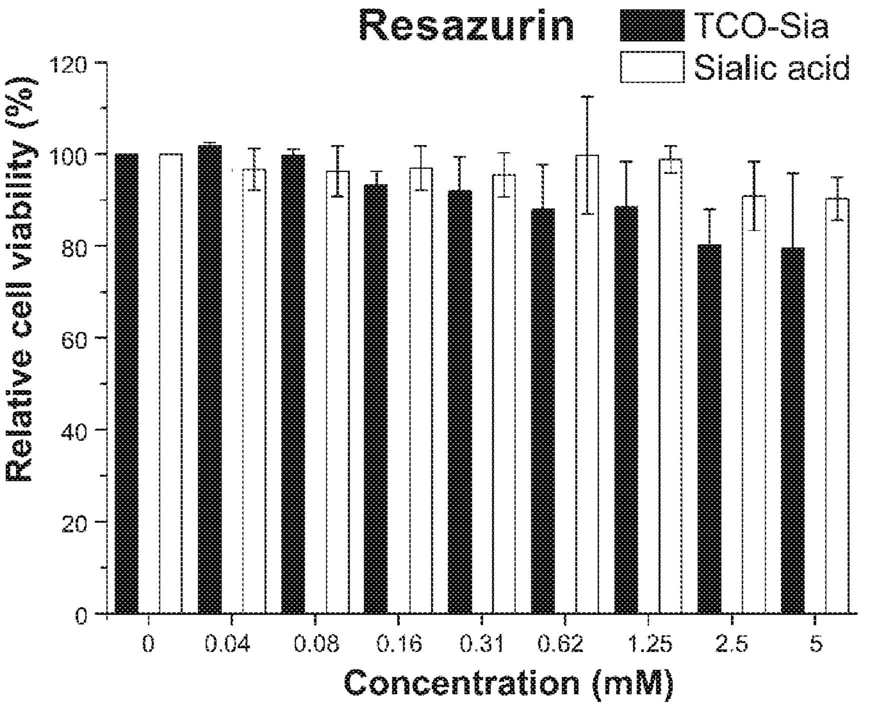

The cell viability was evaluated on U20S cells. Cells seeded at a density of 15 000/well were incubated at 37° C./5% $CO_2$ with TCO-Sia or sialic acid (control) at concentrations ranging from 5 mM to 0 mM for 48 h. The cell metabolic activity was measured by Resazurin/Resorufin assay following the manufacturer's protocol (ThermoFisher Scientific). Briefly: the spent medium was replaced with a fresh one containing a 40 μM concentration of resazurin, and the cells were incubated for 3 hours at 37° C./5% $CO_2$. After this time, the fluorescence of the produced resorufin was measured using a Spark well plate reader (TECAN Ltd.) Cell viability was plotted as % of fluorescence of the untreated cells. Total cell mass was then compared using a crystal violet assay. Briefly, the cells used in the resazurin/resorufin assay were fixed with ice-cold methanol for 10 min at −20° C. Fixed cells were then washed 3× with $H_2O$ and incubated with a 0.1% (w/N) solution of crystal violet for 15 min. Cells were washed after staining 3× with $H_2O$, and the bound dye was dissolved using methanol. Absorbance was measured at 595 nm using a Thermo Multiscan FC spectrophotometer (FIG. 4).

Figure 5:
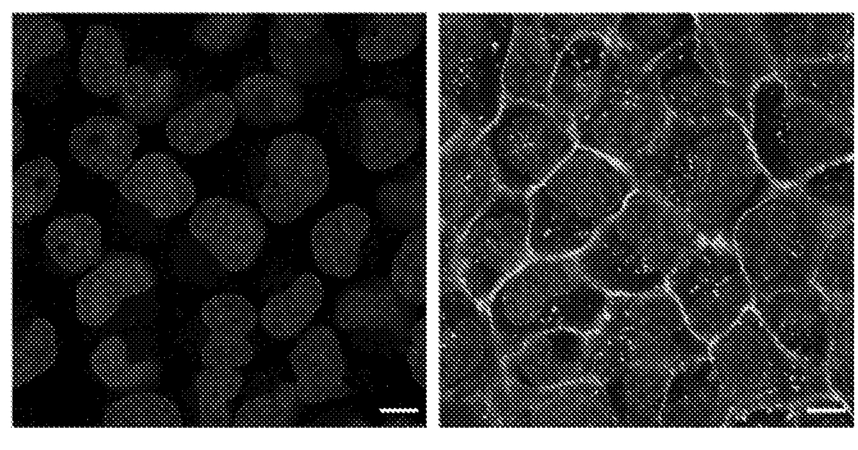
FIG. 5: A) micrograph of U2OS cells acquired using confocal microscope. On the left are cells treated with Cy3-HTz alone, and on the right are cells treated with 1 mM TCO-Sia and Cy3-HTz, the nuclei of the cells were stained with Hoechst nuclear stain. Scale bar 10 μm. B) Overlay histogram showing the cellular fluorescence intensities of control and carbohydrate-treated cells (flow cytometry analysis).
Figure 5:
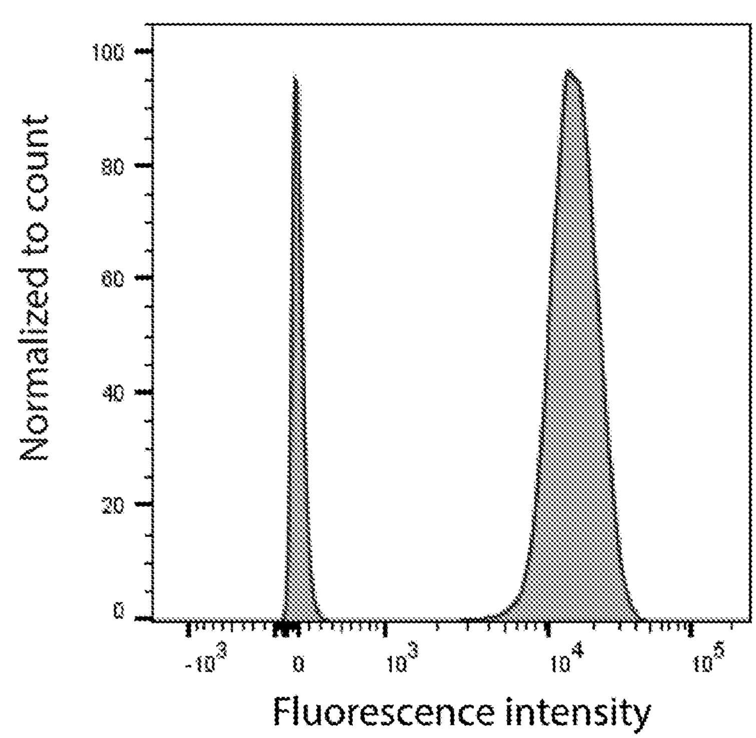

Example 19: Incorporation of TCO-Sia and Labeling with Fluorescent Cy3-HTz Conjugate for Fluorescence Microscopy and FACS Analysis U20S cells were seeded on a 96-well plate (15 000 cells/well). Cells were incubated for 48 h with 1 mM TCO-Sia, after which the cells were washed 3× with DMEM medium (with addition of 10% Fetal bovine serum) and incubated for 30 min with 2.5 μM Sulfo-Cy3-Tetrazine dye (Cy3-HTz, from BroadPharm, BP-23321) in complete DMEM (10% FBS), washed with L15 medium and photographed under a confocal microscope (FIG. 5A). After that, the same cells were detached from the well plate and brought into suspension by the addition of accutase (Thermo, A1110501), and the cellular fluorescence was measured using a flow cytometer (FIG. 5B).

Figure 6:
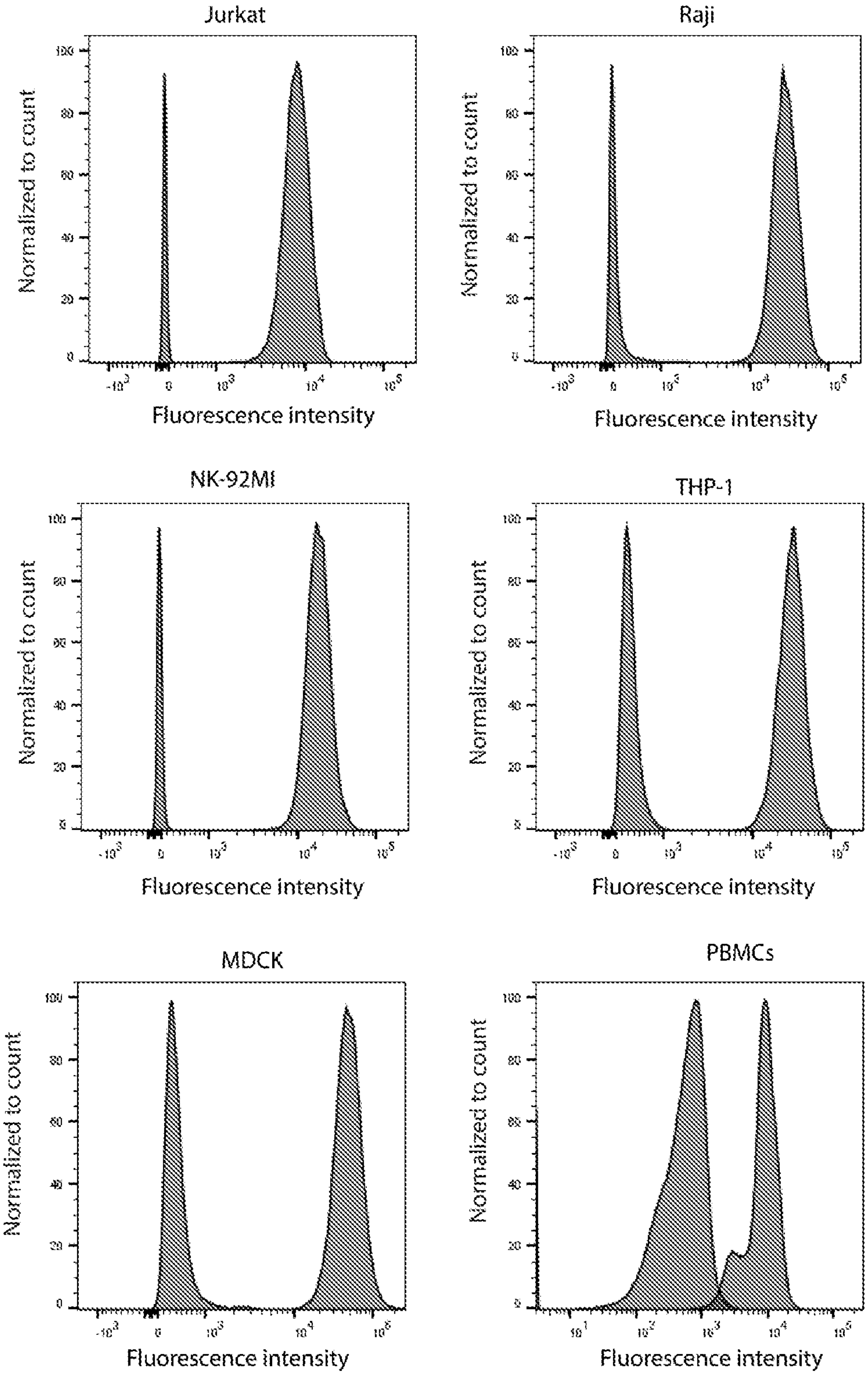
FIG. 6: Incorporation of TCO-Sia into surface proteins of various cell lines followed by labeling with Cy3-HTz. Shown is flow cytometry analysis.

Example 20: Incorporation of TCO-Sia into Cell Surface of Various Cell Lines and Labeling with Fluorescent Cy3-HTz Conjugate for FACS Analysis (Jurkat, Raji, NK92-MI, THP-1 and MDCK) and primary human peripheral blood mononuclear cells (PBMCs). Cells were plated at a concentration of 1 million cells on a 6-well cultivation plate. TCO-Sia was added to a final concentration of 1 mM, and cells were cultivated for 48 h at 37° C./5% $CO_2$, spun down, and washed twice in 1 mL of L15 medium. After the second wash, cells were resuspended in 1 mL of L15 medium and incubated with 2.5 μM Cy3-HTz dye (BroadPharm, BP-23321) for 30 min in a rotator at room temperature. The cells were then washed twice in PBS and measured in a flow cytometer (FIG. 6).

Figure 7:
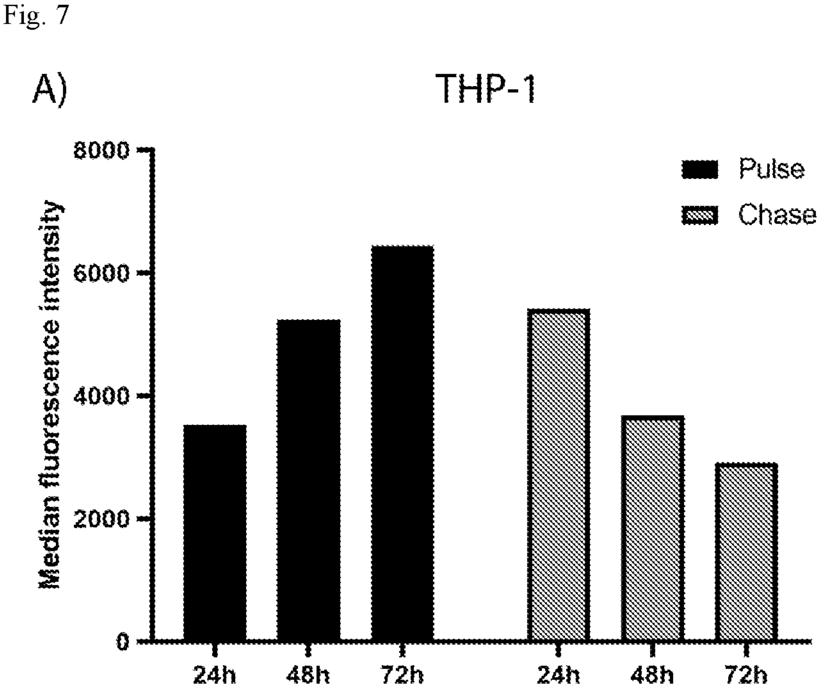
FIG. 7: Persistence of the TCO-Sia on the cell surface in THP-1 and NK-92MI cells detected by labeling with Cy3-HTz.
Figure 7:
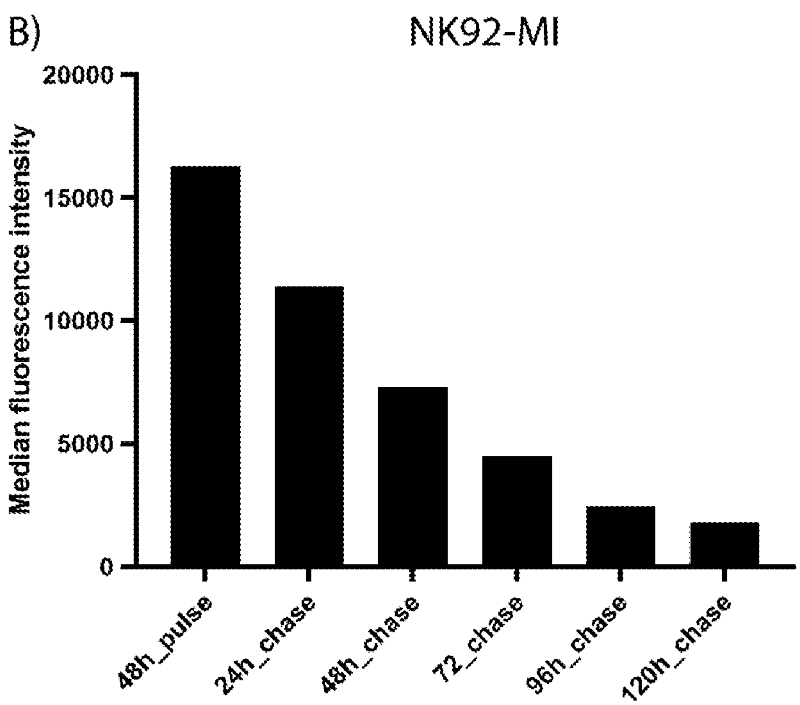

Example 21: Incorporation of TCO-Sia and Persistence of the TCO Modification on the Cell Surface The experiment was performed with THP1-cells seeded at 800 000/well in a 12-well plate. In the "pulse" experiment, cells were pulsed with 1 mM TCO-Sia for 24, 48 and 72 h. At each timepoint, the cells were centrifuged at 300 g/3 min, washed once with 1 mL of L15 medium and resuspended in 1 mL of L15 medium containing 2.5 μM Cy3-HTz (BroadPharm, BP-23321) for 30 min. After this time, cells were washed twice with 1 mL PBS, and a sample of 100 μL was taken, fixed in 4% formaldehyde, and used in flow cytometry analysis. In the "chase" experiment, cells were first pulsed for 72 h with 1 mM TCO-Sia, washed and harvested after 24, 48, and 72 hours after the washout of the sugar. Cells from each timepoint were labeled with Cy3-HTz (BroadPharm, BP-23321) as described above, and fluorescence was measured using a flow cytometer (FIG. 7A).

A similar experiment was performed with NK-92MI cells: 6 million NK-92MI cells were plated in a 6-cm dish in 6 mL of RPMI media (12.5% FBS/12.5% Horse serum) containing 1 mM TCO-Sia and cultivated for 48 h. After this time, cells were washed and split into 6 aliquots and plated on a 12-well plate in fresh medium. After 24, 48, 96 and 120 h, cells were washed once in complete cultivation media and reacted with 2.5 μM Cy3-HTz (BroadPharm, BP-23321) for 30 min, washed twice with PBS, and fixed in 4% formaldehyde solution. Fluorescence intensity was measured using a flow cytometer (FIG. 7B).

IV. Incorporation of TCO-Sia into NK-92MI Cells and Labeling of their Cell Surface with Tetrazine Conjugates In each case, cells were first incubated with 1 mM TCO-Sia for 48 h, washed, and subsequently reacted with the indicated tetrazine conjugate molecule. The presence of the conjugate molecule on the surface of the cells was then detected using various probes (see specific detection method below). The histograms show a clear fluorescence shift in each case when compared to control cells that were incubated with the detection probe, but not with TCO-Sia.

Figure 8:
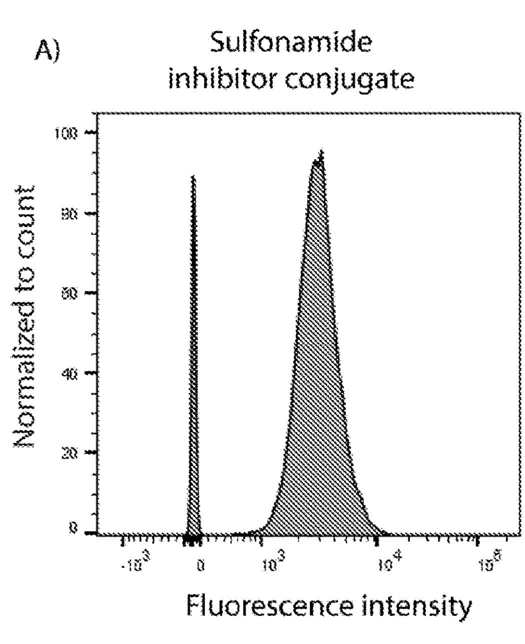
FIG. 8: Flow cytometry analysis of A) NK-92MI cells modified with sulfonamide-PEG3-diPyTz conjugate detected by hCAII-Cy3, B) NK-92MI cells modified with duplex Cy3-Oligonucleotide-HTz conjugate, C) NK-92MI cells modified with NRP-NBD-PEG9-HTz peptide conjugate, D) NK-92MI cells modified with Trastuzumab-HTz conjugate.
Figure 8:
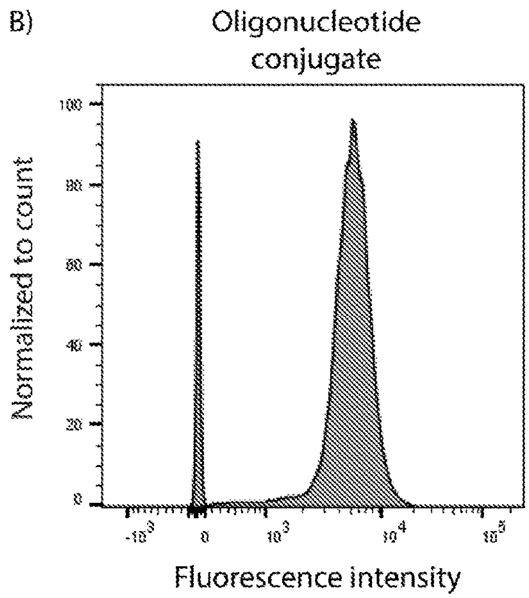
Figure 8:
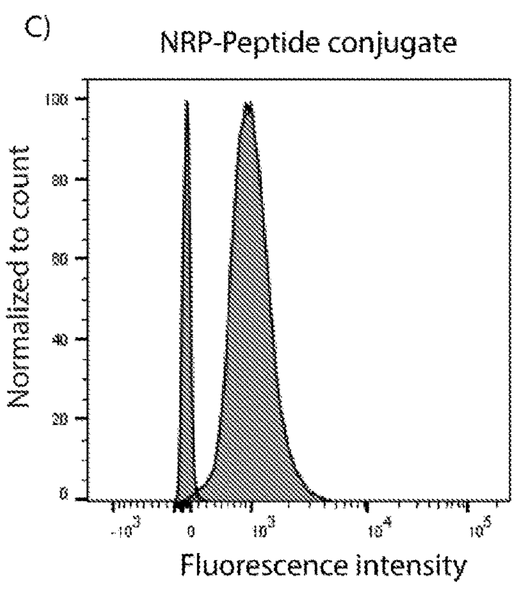
Figure 8:
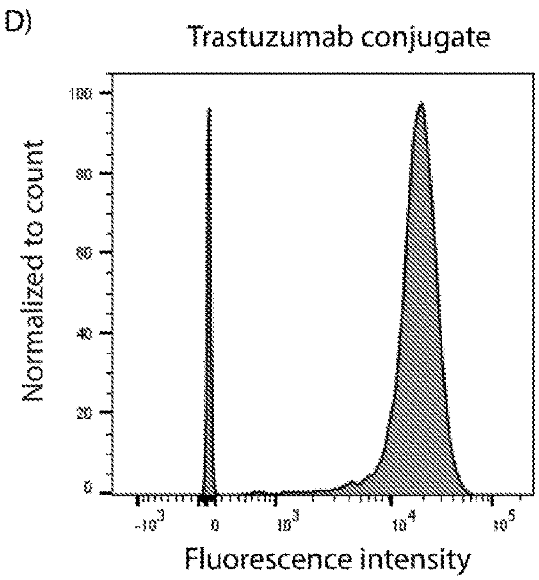

Example 22: Modification of NK-92MI Cells with Sulfonamide-PEG3-diPyTz Conjugate 1000 000 NK-92MI cells previously incubated with 1 mM TCO-Sia for 48 h were washed twice with complete cultivation medium and resuspended in 1 mL of complete cultivation medium. Sulfonamide-PEG3-diPyTz conjugate was added to the cell suspension to a final concentration of 2.5 μM, and cells were incubated for 30 min at room temperature in a rotator. Cells were then washed twice in 1 mL of complete medium and resuspended in PBS. 100 μL of suspension was taken and incubated with Cy3 modified human carbonic anhydrase II (hCAII-Cy3, 0.3 μM final concentration; for its preparation, see procedure below) for 15 minutes to verify that the sulfonamide inhibitor was present on the cell surface. Cells were washed twice in 1 mL PBS, fixed with 4% formaldehyde, and the cellular fluorescence was measured using a flow cytometer (FIG. 8A). Control cells were processed in the same way, except that they were not treated with the Sulfonamide-PEG3-diPyTz conjugate.

Preparation of human carbonic anhydrase II Cy3 conjugate (hCAII-Cy3): 100 μL of recombinant human Carbonic anhydrase II (hCAII, 34 μM, kindly provided by P. Rezacova's group, IOCB, Prague) was transferred into 0.2 M bicarbonate buffer, pH 9, using aZeba spin desalting column (Thermo cat. no. 89882). A 10× (molar) excess of Cy3-NHS ester (Lumiprobe cat. no. 11020) was added to the hCAII solution, and the mixture was incubated for 1 hour at room temperature with constant shaking. After that, the sample was spun down at 11000 RPM/1 minute to pellet any insoluble material. To remove the unreacted dye, the reaction mixture was passed through a Zeba desalting column preconditioned in 1× concentrated phosphate-buffered saline (PBS) to obtain hCAII-Cy3 conjugate.

Example 23: Modification of NK-92MI Cells with Cy3-Oligonucleotide-HTz Conjugate 1000 000 NK-92MI cells previously incubated with 1 mM TCO-Sia for 48 h were washed twice with complete cultivation medium and resuspended in 0.5 mL of complete cultivation medium containing 2.5 μM Cy3-Oligonucleotide-HTz conjugate. Cells were incubated on a rotating wheel at room temperature for 30 minutes, washed twice with PBS, and a 50 μl aliquot was fixed with 4% formaldehyde. Cellular fluorescence was measured using a flow cytometer (FIG. 8B). The fluorescence intensity of oligonucleotide-modified cells was compared to the control sample processed in the same way except for prior incubation with TCO-Sia.

Example 24: Modification of NK-92MI Cells with Fluorescent NRP-NBD-PEG9-HTz Peptide Conjugate 1000 000 NK-92MI cells previously incubated with 1 mM TCO-Sia for 48 h were washed twice with complete cultivation medium to remove the unincorporated TCO, and resuspended in 1 mL of complete cultivation medium containing 2.5 μM NRP-NBD-PEG9-HTz peptide conjugate. Cells were incubated on a rotating wheel at room temperature for 30 minutes, washed twice with PBS, and a 100 μl aliquot was fixed with 4% formaldehyde. The cellular fluorescence of the fixed cells was measured using a flow cytometer (FIG. 8C). This conjugate can be detected by fluorescence due to the presence of the NBD dye. The fluorescence intensity of the modified cells was compared to control sample cells processed in the same way except for prior incubation with TCO-Sia.

Example 25: Modification of NK-92MI Cells with Trastuzumab-HTz Conjugate 1000 000 NK-92MI cells previously incubated with 1 mM TCO-Sia for 48 h were washed twice with complete cultivation medium to remove the unincorporated TCO-Sia, and cells were resuspended in 0.5 mL of complete cultivation medium containing 0.34 μM Trastuzumab-HTz conjugate. Cells were incubated on a rotating wheel at room temperature for 30 minutes, and were washed twice with PBS. To detect the antibody immobilized on the surface of NK-92MI cells, a 100 μl aliquot was incubated with a goat anti-human secondary antibody (Thermo, cat. No. SA5-10135, DyLight 550 conjugate, 0.5 μg/mL) for 15 min, washed twice, and the cells were fixed with 4% formaldehyde. The cellular fluorescence of the fixed cells was measured using a flow cytometer (FIG. 8D). The fluorescence intensity of antibody-modified cells was compared to the control sample processed in parallel but lacking the TCO-Sia modification.

Example 26: Incorporation of TCO-Sia into Cell Surface and Labeling with Various Fluorophore Tz Conjugates (Microscopy Analysis)

Figure 9:
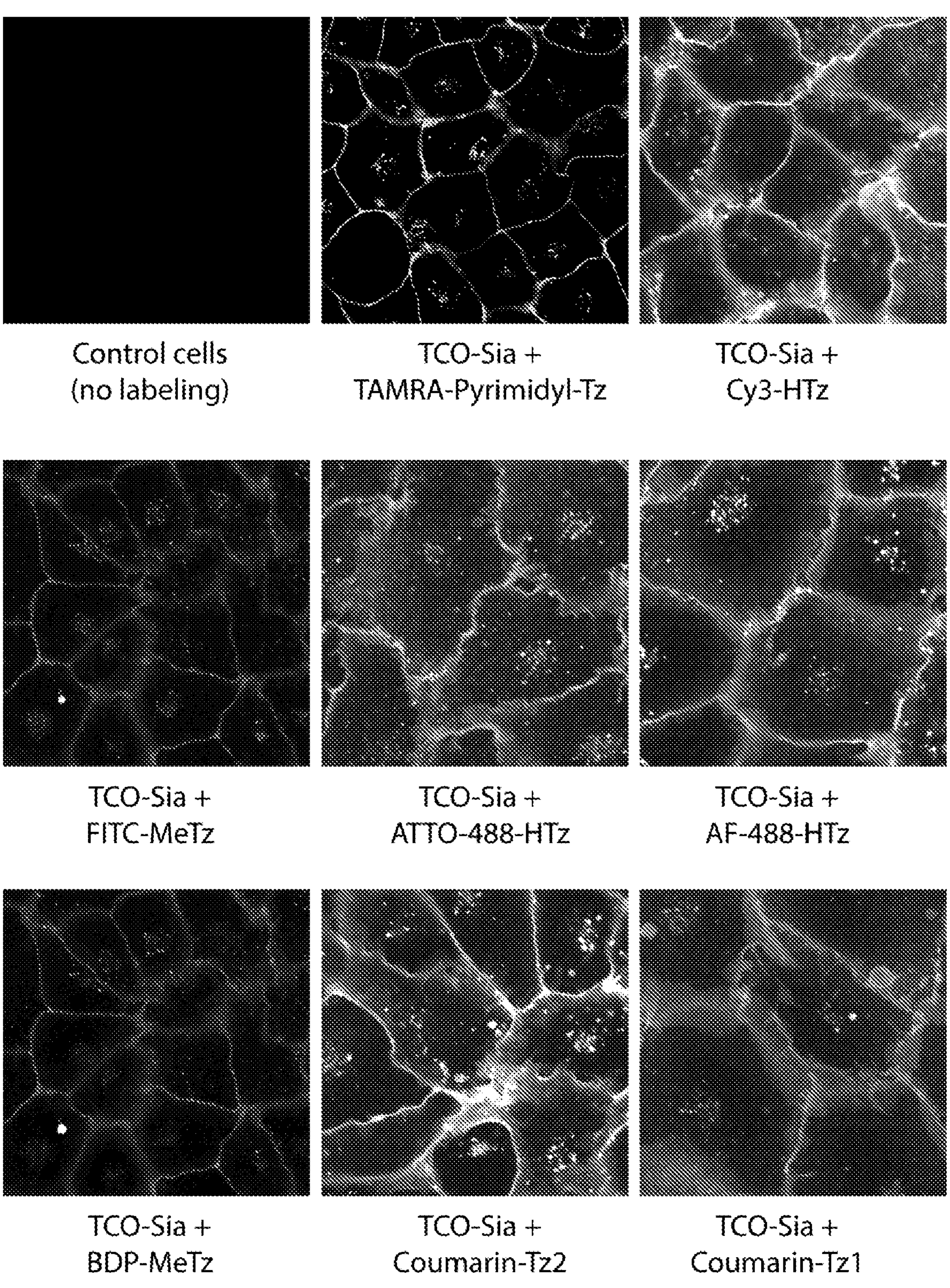
FIG. 9: A) micrograph of U2OS cells acquired using confocal microscope. Cells were treated with 1 mM TCO-Sia and eight different Tz-dye conjugates. Control cells are unlabeled cells.

U2OS cells were seeded on a 96-well plate (15 000 cells/well). Cells were incubated for 48 h with 1 mM TCO-Sia, after which the cells were washed 3× with DMEM medium (with addition of 10% Fetal bovine serum) and incubated for 30 min with or without (control cells) 2.5 μM tetrazine conjugates in complete DMEM (10% FBS), washed with L15 medium and photographed under a confocal microscope. The following compounds were used: TAMRA-Pyrimidyl-Tz (Jena Bioscience, CLK-097), Cy3-HTz (BroadPharm, BP-23321), FITC-MeTz, ATTO-488-HTz (Jena Bioscience, CLK-010-02), AF-488-HTz (Click Chemistry Tools, 1361-1), BDP-MeTz, Coumarin-Tz2 and Coumarin-Tz1 (FIG. 9).

Figure 10:
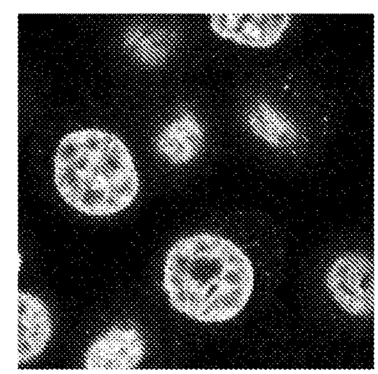
FIG. 10: A) micrograph of PC3 cells acquired using confocal microscope. Cells were treated with 1 mM TCO-Sia followed by addition of MeTz-PEG3-PEG3-biotin-PEG3-DBCO conjugate, then Cy3-azide and finally with fluorescent streptavidin. The nuclei of the cells were stained with Hoechst nuclear stain.
Figure 10:
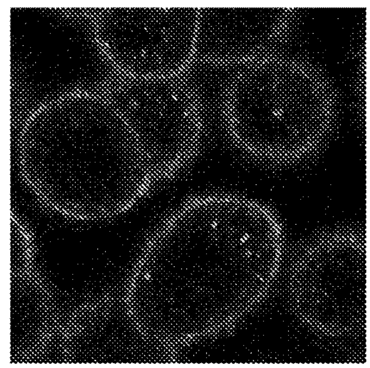
Figure 10:
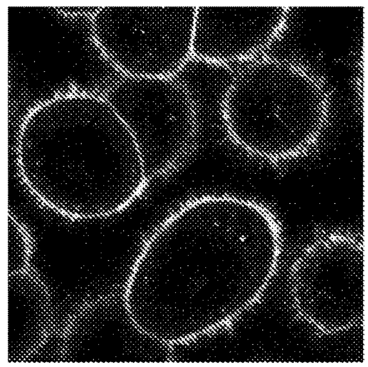

Example 27: Incorporation of TCO-Sia into Cell Surface and Labeling with MeTz-PEG3-PEG3-Biotin-PEG3-DBCO Conjugate Followed by Double Labeling with Fluorophore and Protein PC3 cells were seeded on a 96-well plate cultivation dishes (15000 cells/well) and incubated for 48 h with 1 mM TCO-Sia in high glucose DMEM medium supplemented with 10% FBS (Thermo) and 0.1 mg/mL of penicillin-streptomycin at 37° C./5% $CO_2$, after which the cells were washed 3× with DMEM medium (with addition of 10% Fetal bovine serum) and incubated for 1 hour with Cy3-azide (Lumiprobe, A1330) to label the DBCO moiety of the MeTz-PEG3-PEG3-biotin-PEG3-DBCO conjugate on the cell surface. Cells were washed with L15 medium, and photographed under a confocal microscope. The, cells were incubated with streptavidin (Thermo 12-4317-87), washed with L15 medium and photographed under a confocal microscope (FIG. 10).

Figure 11:
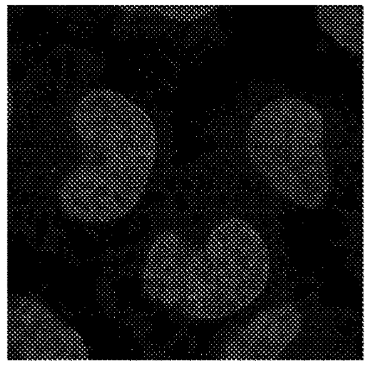
FIG. 11: A) micrograph of HeLa cells acquired using confocal microscope. Cells were treated with 1 mM TCO-Sia followed by addition of FLAG-MeTz peptide conjugate or without addition of FLAG-MeTz peptide conjugate as a control. Then, fluorescent anti-FLAG antibody was added. The nuclei of the cells were stained with Hoechst nuclear stain.
Figure 11:
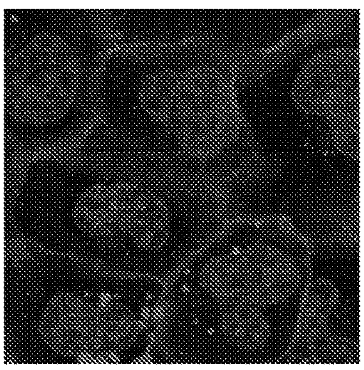

Example 28: Incorporation of TCO-Sia into Cell Surface and Labeling with FLAG-MeTz Peptide Conjugate HeLa cells were seeded on a 96-well plate cultivation dishes ($2\times10^4$ cells/well) and incubated for 48 h with 1 mM TCO-Sia in high glucose DMEM medium supplemented with 10% FBS (Thermo) and 0.1 mg/mL of penicillin-streptomycin at 37° C./5% $CO_2$, after which the cells were washed 3× with DMEM medium (with addition of 10% Fetal bovine serum) and incubated for 1 hour with or without (control cells) 5 μM FLAG-MeTz peptide conjugate (prepared as previously described in La-Venia et al. Chemistry A European Journal 27(54), 13632, 2021) in complete DMEM (10% FBS), washed with L15 medium, incubated with anti-FLAG antibody (Thermo, MA1-91878-D488) and photographed under a confocal microscope. The nuclei were stained with Hoechst nuclear stain (FIG. 11).

Figure 12:
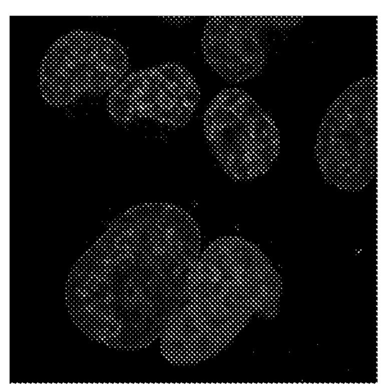
FIG. 12: A) micrograph of HeLa cells acquired using confocal microscope. Cells were treated with 1 mM TCO-Sia followed by addition of Biotin-PEG3-diPy-Tz conjugate or without addition of Biotin-PEG3-diPy-Tz conjugate as a control. Then, fluorescent streptavidin was added. The nuclei of the cells were stained with Hoechst nuclear stain.
Figure 12:
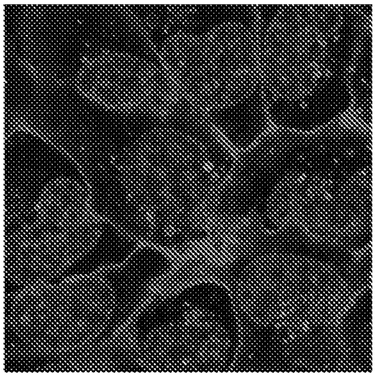

Example 29: Incorporation of TCO-Sia into Cell Surface and Labeling with Biotin-PEG3-diPy-Tz Conjugate HeLa cells were seeded on a 96-well plate cultivation dishes ($2\times10^4$ cells/well) and incubated for 48 h with 1 mM TCO-Sia in high glucose DMEM medium supplemented with 10% FBS (Thermo) and 0.1 mg/mL of penicillin-streptomycin at 37° C./5% $CO_2$, after which the cells were washed 3× with DMEM medium (with addition of 10% Fetal bovine serum) and incubated for 30 min with or without (control cells) 2.5 μM Biotin-PEG3-diPy-Tz conjugate in complete DMEM (10% FBS). Cells were then washed with L15 medium, incubated with streptavidin (Thermo 12-4317-87) and photographed under a confocal microscope. The nuclei were stained with Hoechst nuclear stain (FIG. 12).

Figure 13:
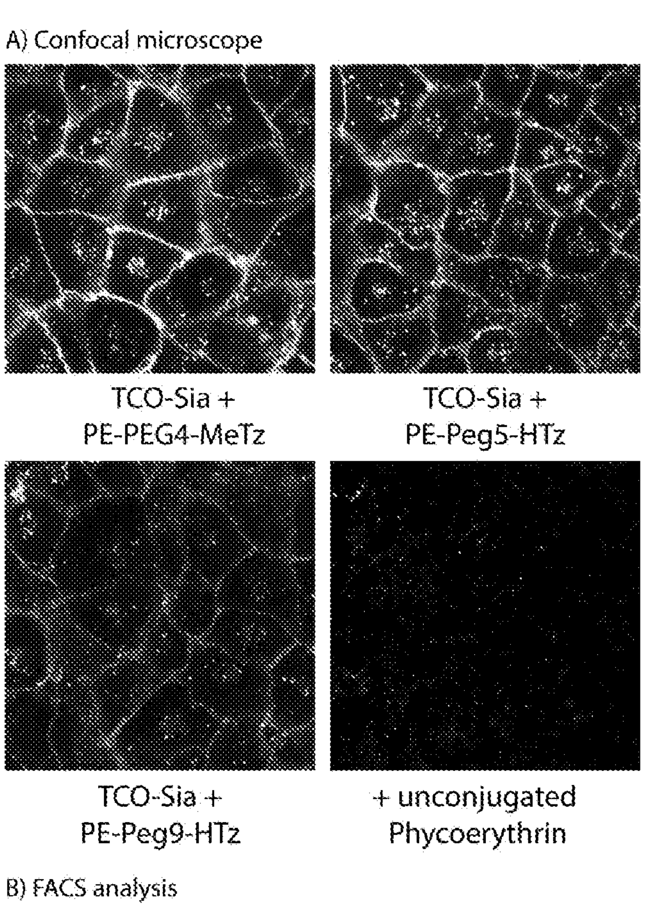
FIG. 13: A) micrograph of U2OS cells acquired using confocal microscope. A) cells were treated with 1 mM TCO-Sia and labeled with three different phycoerythrin-Tz conjugates. B) histograms of the same cells acquired by flow cytometry analysis.
Figure 13:
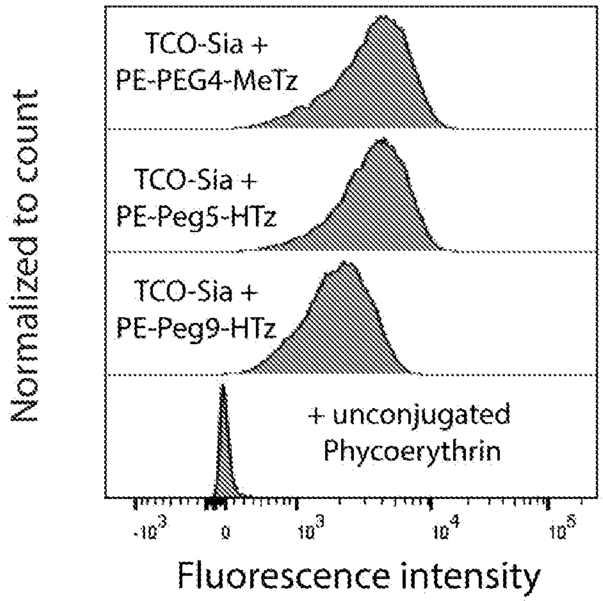
Figure 14:
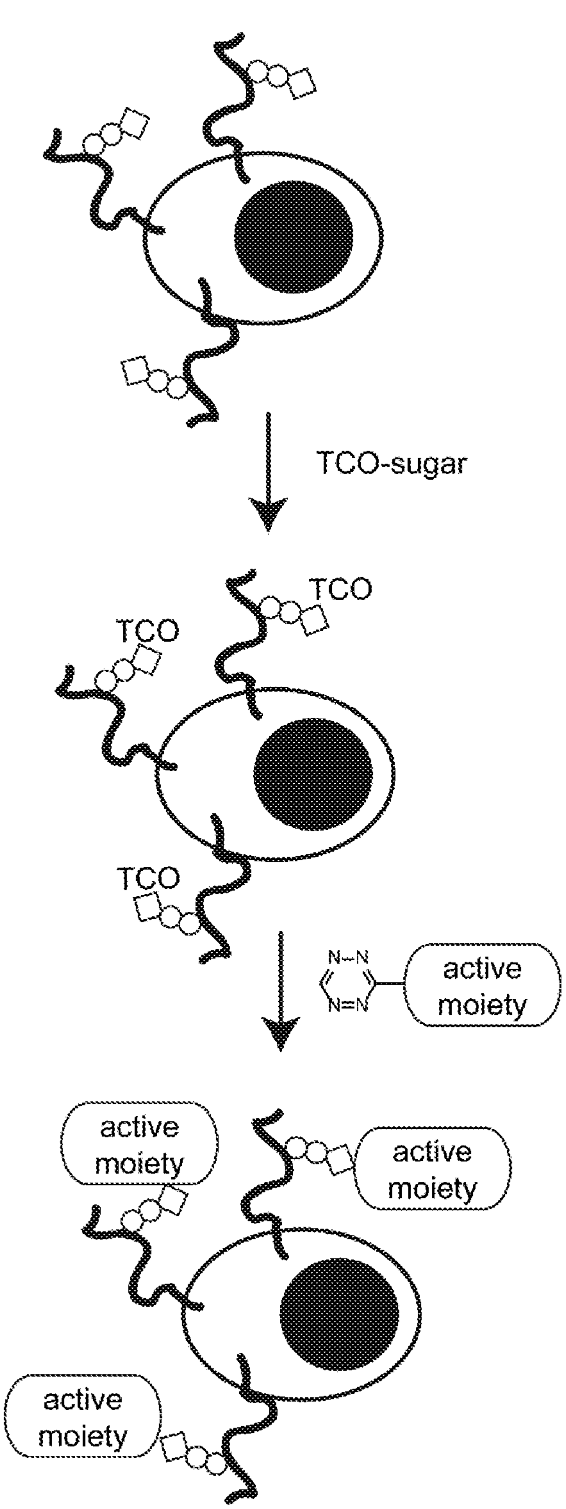
FIG. 14: Schematic illustration of the presented procedure for the modification of cell surfaces with various active molecules. The cells are shown as oval shape and the black sphere represents cellular nucleus.

Example 30: Incorporation of TCO-Sia into Cell Surface and Labeling with PE-Tetrazine Conjugates U2OS cells were seeded on a 96-well plate (15 000 cells/well). Cells were incubated for 48 h with 1 mM TCO-Sia, after which the cells were washed 3× with DMEM medium (with addition of 10% Fetal bovine serum) and incubated for 2 hours with 5 μM PE-PEG4-MeTz or 5 μM PE-PEG5-HTz or 5 μM PE-PEG9-HTz conjugates or with 5 μM unconjugated Phycoerythrin as a control in complete DMEM (10% FBS). Cells were then washed with L15 medium and photographed under a confocal microscope (FIG. 13).

INDUSTRIAL APPLICABILITY

The provided procedure can be used to attach different active moieties to the cell surface of various cell lines. The additional active moiety provides the cells with a new function, property, or alters the cell surface structure. Depending on the intended application, the resulting cell-surface modified cells can be used in bioimaging, for the construction of biomaterials, in regenerative medicine, as drug delivery systems, in immunotherapy and other biomedical applications. The preferred examples include the use of the cell surface-modified cells to direct therapeutic cells to a specific location in the body (e.g. immune cells to cancer), the use of the modified cells as drug delivery carriers, the use of the modified cells as carriers of fluorescent, radiolabel or other biophysical imaging probes, the protection of cells by the active moiety from unwanted interactions, or for promoting cellular interactions by the active moiety.

The invention claimed is:

1. A method for binding active moieties to a cell surface comprising the following steps:

a) the cells are co-cultured with at least one carbohydrate derivative of general formula I

I

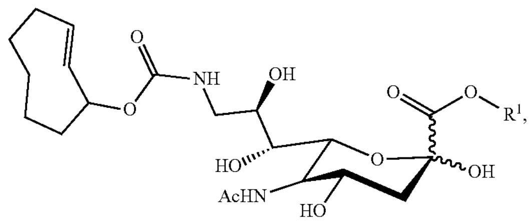

wherein $R^1$ is selected from H and $C_{1-6}$ linear or branched alkyl, to form trans-cyclooctene presenting cells;

b) at least one 1,2,4,5-tetrazine conjugate of general formula II

II

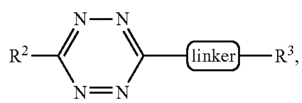

wherein $R^2$ is selected from: H, $C_{1-10}$ alkyl, $C_{6-10}$ aryl, 5-10-membered heteroaryl, $C_{1-10}$ alkoxy, $C_{6-10}$aryl-$C_{1-10}$alkyl, 5-10-membered heteroaryl-$C_{1-10}$ alkyl;

linker is selected from $C_{1-10}$ alkylene, $C_{6-10}$ arylene, 5-10-membered heteroarylene, $C_{6-10}$aryl-$C_{1-10}$alkylene, 5-10-membered heteroaryl-$C_{1-10}$alkylene, and polyethylene glycol;

$R^3$ is an active moiety selected from fluorophore, inhibitor, ligand, oligonucleotide, peptide, protein, enzyme, antibody, single-domain antibody, polymer, and nanoparticle;

is brought into contact with the trans-cyclooctene presenting cells in order to covalently attach the active moiety to the cell surface.

2. The method according to claim 1, wherein the reaction in step b) between trans-cyclooctene groups on the cell surface of the trans-cyclooctene presenting cells and the tetrazine conjugate of general formula II is carried out at a temperature within the range of room temperature to 37° C. in a cell culturing medium or in a biologically acceptable buffer.

3. The method according to claim 1, wherein the cells to be co-cultured with the carbohydrate derivative of general formula I are selected from cancer cells, epithelial cells, endothelial cells, fibroblasts, stem cells, immune cells, macrophages, blood cells and monocytes.

4. A carbohydrate derivative of general formula I:

I

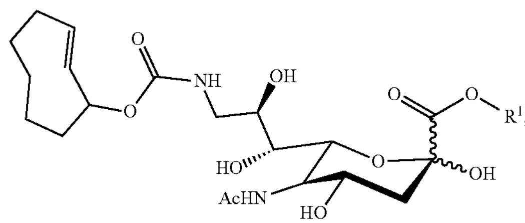

wherein $R^1$ is selected from H and $C_{1-6}$ linear or branched alkyl.

5. The carbohydrate derivative according to claim 4, wherein the C—O bond between the trans-cyclooctene and the carbamate is axial.

6. A method, comprising binding active moieties to cell surfaces in vitro and/or in vivo for therapeutic purposes using the carbohydrate derivative of general formula I according to claim 4.

7. A method, comprising covalently binding active moieties to cell surfaces in vitro using the carbohydrate derivative of general formula I according to claim 4.

8. A kit containing at least one carbohydrate derivative of general formula I according to claim 4, and at least one 1,2,4,5-tetrazine conjugate of general formula II

II

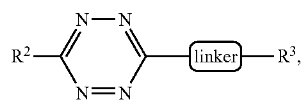

wherein $R^2$ is selected from: H, $C_{1-10}$ alkyl, $C_{6-10}$ aryl, 5-10-membered heteroaryl, $C_{1-10}$ alkoxy, $C_{6-10}$aryl-$C_{1-10}$alkyl, 5-10-membered heteroaryl-$C_{1-10}$alkyl;

linker is selected from $C_{1-10}$ alkylene, $C_{6-10}$ arylene, 5-10-membered heteroarylene, $C_{6-10}$aryl-$C_{1-10}$alkylene, 5-10-membered heteroaryl-$C_{1-10}$alkylene, and polyethylene glycol;

$R^3$ is an active moiety selected from fluorophore, inhibitor, ligand, oligonucleotide, peptide, protein, enzyme, antibody, single-domain antibody, polymer, and nanoparticle.

9. The kit containing at least one carbohydrate derivative of general formula I according to claim 4, cells amenable to modification by the carbohydrate derivative(s), and at least one 1,2,4,5-tetrazine conjugate of general formula II

II

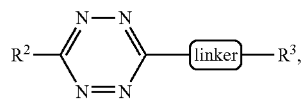

wherein $R^2$ is selected from: H, $C_{1-10}$ alkyl, $C_{6-10}$ aryl, 5-10-membered heteroaryl, $C_{1-10}$ alkoxy, $C_{6-10}$aryl-$C_{1-10}$alkyl, 5-10-membered heteroaryl-$C_{1-10}$alkyl;

linker is selected from $C_{1-10}$ alkylene, $C_{6-10}$ arylene, 5-10-membered heteroarylene, $C_{6-10}$aryl-$C_{1-10}$alkylene, 5-10-membered heteroaryl-$C_{1-10}$alkylene, and polyethylene glycol;

$R^3$ is an active moiety selected from fluorophore, inhibitor, ligand, oligonucleotide, peptide, protein, enzyme, antibody, single-domain antibody, polymer, and nanoparticle.

10. The kit according to claim 9, wherein the cells amenable to modification by the carbohydrate derivative(s) are selected from cancer cells, epithelial cells, endothelial cells, fibroblasts, stem cells, immune cells, macrophages, blood cells and monocytes.

* * * * *